(12) United States Patent
Ogawa et al.

(10) Patent No.: US 11,046,980 B2
(45) Date of Patent: Jun. 29, 2021

(54) METHOD FOR PRODUCING RARE FATTY ACID USING NOVEL ENZYME, AND NOVEL RARE FATTY ACID

(71) Applicants: KYOTO UNIVERSITY, Kyoto (JP); Noster Inc., Muko (JP)

(72) Inventors: Jun Ogawa, Kyoto (JP); Shigenobu Kishino, Kyoto (JP); Teruo Kawada, Kyoto (JP); Nobuyuki Takahashi, Kyoto (JP); Tsuyoshi Goto, Kyoto (JP); Yasunori Yonejima, Muko (JP)

(73) Assignees: KYOTO UNIVERSITY, Kyoto (JP); Noster, Inc., Muko (JP)

( * ) Notice: Subject to any disclaimer, the term of this patent is extended or adjusted under 35 U.S.C. 154(b) by 0 days.

(21) Appl. No.: 16/404,241

(22) Filed: May 6, 2019

(65) Prior Publication Data

US 2019/0256876 A1  Aug. 22, 2019

Related U.S. Application Data

(62) Division of application No. 15/113,604, filed as application No. PCT/JP2015/051842 on Jan. 23, 2015, now abandoned.

(30) Foreign Application Priority Data

Jan. 24, 2014 (JP) .................................. 2014-011855

(51) Int. Cl.
| | |
|---|---|
| *C07C 59/42* | (2006.01) |
| *C12P 7/64* | (2006.01) |
| *C12N 9/02* | (2006.01) |
| *C12P 7/42* | (2006.01) |
| *C12N 9/04* | (2006.01) |

(52) U.S. Cl.
CPC ............ *C12P 7/6409* (2013.01); *C07C 59/42* (2013.01); *C12N 9/0006* (2013.01); *C12N 9/0069* (2013.01); *C12P 7/42* (2013.01); *C12P 7/6427* (2013.01)

(58) Field of Classification Search
None
See application file for complete search history.

(56) References Cited

U.S. PATENT DOCUMENTS

| 9,611,238 B2 | 4/2017 | Serhan et al. |
|---|---|---|
| 2005/0112612 A1 | 5/2005 | Klaenhammer et al. |
| 2013/0315849 A1 | 11/2013 | Farwick et al. |
| 2015/0125911 A1 | 5/2015 | Ogawa et al. |
| 2015/0342916 A1 | 12/2015 | Ogawa et al. |
| 2016/0000739 A1 | 1/2016 | Ogawa et al. |

FOREIGN PATENT DOCUMENTS

| EP | 1197560 A1 | 4/2002 |
|---|---|---|
| JP | 2006-525805 A | 11/2006 |
| JP | 2007-252333 A | 10/2007 |
| JP | 2007-259712 A | 10/2007 |
| JP | 2011-184411 A | 9/2011 |
| WO | WO 2004/005442 A1 | 1/2004 |
| WO | WO 2013/168310 A1 | 11/2013 |
| WO | WO 2014/069227 A1 | 5/2014 |
| WO | WO 2014/129384 A1 | 8/2014 |

OTHER PUBLICATIONS

H. Kobayashi et al. "Comparative study of the product components of lipid oxidation in aqueous and organic systems", Chemistry and Physics of Lipids 126: 111-120. (Year: 2003).*
U.S. Appl. No. 15/113,604, filed Jul. 22, 2016.
Ha et al., "Anticarcinogens from fried ground beef: heat-altered derivatives of linoleic acid," *Carcinogenesis*, 8(12): 1881-1887 (1987).
Hirata et al., "Cloning and functional analysis of linoleic acid Δ12 hydratase from *Lactobacillus acidophilus*," *Abstracts of the Annual Conference of the Society for Biotechnology*, Japan, 66: 80, abstract 1P-248 (2014).
Ip et al., "Mammary Cancer Prevention by Conjugated Dienoic Derivative of Linoleic Acid," *Cancer Research*, 51(22): 6118-6124 (1991).
Joo et al., "Biochemical characterization and FAD-binding analysis of oleate hydratase from *Macrococcus caseolyticus*," *Biochimie*, 94(3): 907-915 (2012).
Kim et al., "9-oxo-10(E),12(E)-octadecadienoic acid derived from tomato is a potent PPARα agonist to decrease triglyceride accumulation in mouse primary hepatocytes," *Mol. Nutr. Food. Res.*, 55(4): 585-593 (2011).
Kim et al., "Potent PPARα Activator Derived from Tomato Juice, 13-oxo-9,11-Octadecadienoic Acid, Decreases Plasma and Hepatic Triglyceride in Obese Diabetic Mice," *PLoS One*, 7(2): e31317 (2012).
Kishimoto et al., "Two Distinct Pathways for the Formation of Hydroxy FA from Linoleic Acid by Lactic Acid Bacteria," *Lipids*, 38(12): 1269-1274 (2003).
Lee, "Conjugated linoleic acid and atherosclerosis in rabbits," *Atherosclerosis*, 108(1): 19-25 (1994).
Oh et al., "Biotransformation of Linoleic Acid into Hydroxy Fatty Acids and Carboxylic Acids Using a Linoleate Double Bond Hydratase as Key Enzyme," *Adv. Synth. Catal.*, 357: 408-416 (Jan. 19, 2015).
Takeuchi et al., "Functional analysis of linoleate hydratase from *Lactobacillus plantarum* AKU 1009a," *Abstracts of the Annual Conference of the Society for Biotechnology*, Japan, 65: 113, abstract 2P-037 (2013).

(Continued)

*Primary Examiner* — Rebecca E Prouty
(74) *Attorney, Agent, or Firm* — Leydig, Voit & Mayer, Ltd.

(57) ABSTRACT

The present invention provides production of hydroxylated fatty acid by a hydration reaction using a novel enzyme derived from *Lactobacillus* and using fatty acid as a substrate, and further, a production method of oxo fatty acid by an enzyme reaction or chemical oxidation reaction using the hydroxylated fatty acid as a substrate. In addition, a valuable novel rare fatty acid obtained by such production method is also provided.

5 Claims, 2 Drawing Sheets

Specification includes a Sequence Listing.

(56) References Cited

OTHER PUBLICATIONS

Volkov et al., "Crystal structure analysis of a fatty acid double-bond hydratase from *Lactobacillus acidophilus*," *Acta Crystallographica Section D, Biological Crystallography*, 69(4): 648-657 (2013).
Japanese Patent Office, International Search Report in International Patent Application No. PCT/JP2015/051842 (dated Apr. 21, 2015).
European Patent Office, Supplementary Partial European Search Report in European Patent Application No. 15740644 (dated Jun. 22, 2017).

* cited by examiner

METHOD FOR PRODUCING RARE FATTY ACID USING NOVEL ENZYME, AND NOVEL RARE FATTY ACID

CROSS-REFERENCE TO RELATED APPLICATIONS

This patent application is a divisional of copending U.S. patent application Ser. No. 15/113,604, filed on Jul. 22, 2016, now abandoned, which is the U.S. national phase of International Patent Application No. PCT/JP2015/051842, filed on Jan. 23, 2015, which claims the benefit of Japanese Patent Application No. 2014-011855, filed Jan. 24, 2014, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 14,459 bytes ASCII (Text) file named "726078SequenceListing.txt," created May 2, 2019.

TECHNICAL FIELD

The present invention relates to a production method of a fatty acid. More particularly, the present invention relates to a production of a hydroxylated fatty acid by using an unsaturated fatty acid as a starting material, which is characterized by a hydration reaction by a novel enzyme, and further relates to a production of an oxo fatty acid from hydroxylated fatty acid by an enzyme reaction or chemical oxidation reaction. In addition, it relates to a novel rare fatty acid obtained by the production method.

BACKGROUND ART

Conjugated fatty acid represented by conjugated linoleic acid (CLA) has been reported to have various physiological activities such as a lipid metabolism improving effect, an anti-arteriosclerosis action, a body fats decreasing action and the like (non-patent documents 1-3), and is a functional lipid expected to be applicable to various fields of medicament, functional food and the like (patent documents 1, 2). While CLA is known to be contained in dairy products and meat products since it is produced by microorganisms present in the stomach of ruminant and to be present in a small amount in vegetable oil, the detailed mechanism of production thereof is not known.

The present inventors reported that enzymes present in the fungus of *Lactobacillus plantarum* (CLA-HY, CLA-DC, CLA-DH) are essential for the reaction to convert linoleic acid to conjugated linoleic acid (patent document 1). The mechanism of a series of specific reactions, the presence of an intermediate and the like in these enzyme reactions have been reported (patent document 4). While these enzyme reactions were effective for the production of a rare fatty acid having a hydroxyl group, a carbonyl group at the 10-position of an unsaturated fatty acid having 18 carbon atoms such as linoleic acid and the like, a production method of a rare fatty acid having a hydroxyl group, a carbonyl group at the 13-position has not been clarified.

In addition, it has been reported in recent years that oxo fatty acids such as 9-oxo-octadecadienoic acid, 13-oxo-octadecadienoic acid and the like contained in tomato have an activity to improve lifestyle-related diseases, such as lipid metabolism improvement and the like (patent document 3, non-patent documents 4, 5). Furthermore, hydroxylated fatty acid and oxo fatty acid having a hydroxyl group, an oxo group at the 10-position have been reported to have an activity to improve lifestyle-related diseases, such as metabolism improvement, lipid metabolism improvement and the like, and an activity to improve the intestine barrier function (patent documents 5, 6), hydroxylated fatty acid and oxo fatty acid are drawing an increasing attention. However, synthesis of functional hydroxylated fatty acid, functional oxo fatty acid from unsaturated fatty acid is difficult since, in hydroxylated fatty acid and oxo fatty acid, it is necessary to distinguish double bonds present in a plurality in a molecule of unsaturated fatty acid and introduce hydroxyl group, carbonyl group into particular positions.

DOCUMENT LIST

Patent Documents patent document 1: JP-A-2007-259712
patent document 2: JP-A-2007-252333
patent document 3: JP-A-2011-184411
patent document 4: WO 2013/168310
patent document 5: WO 2014/069227
patent document 6: WO 2014/129384

Non-Patent Documents non-patent document 1: Ha Y L, (1987), Carcinogenesis, vol. 8, no. 12, p. 1881-1887
non-patent document 2: Clement Ip, (1991), Cancer Res., vol. 51, p. 6118-6124
non-patent document 3: Kisun N L, (1994), Atherosclerosis, vol. 108, p. 19-25
non-patent document 4: Kim Y-I, (2011), Mol. Nutr. Food Res., vol. 55, p. 585-593
non-patent document 5: Kim Y-I, (2012), PLoS ONE, vol. 7, no. 2, e31317

SUMMARY OF THE INVENTION

Problems to be Solved by the Invention

An object of the present invention is to provide a method of producing hydroxylated fatty acid, oxo fatty acid by using unsaturated fatty acid as a starting material and using a novel enzyme.

Means of Solving the Problems

The present inventors have clarified a reaction wherein *Lactobacillus acidophilus* hydroxylates the 13-position of an unsaturated fatty acid having 18 carbon atoms and identified a novel enzyme (FA-HY) involved in the production.

The present inventors have found a method of converting unsaturated fatty acid having 16, 18, 20 carbon atoms, cis-4, cis-7, cis-10, cis-13, cis-16, cis-19-docosahexaenoic acids (DHA) and cis-9-tetradecenoic acid (myristoleic acid) to hydroxylated fatty acid by using a novel enzyme (FA-HY), and further, a method of oxidizing a hydroxyl group of the produced substance by an enzyme reaction or chemical reaction.

The present inventor have produced found hydroxylated fatty acid and oxo fatty acid having a structure not found heretofore, by a production method of a new rare fatty acid by using a novel enzyme (FA-HY), and found that they have a nuclear receptor PPARα and PPARγ agonist activity.

To be specific, the present inventors have found that 13-hydroxy-cis-9-octadecenoic acid is produced from linoleic acid by using a novel enzyme (FA-HY), and further found that 13-oxo-cis-9-octadecenoic acid is produced from 13-hydroxy-cis-9-octadecenoic acid by introducing an enzyme reaction or a chemical oxidation method using chromic acid.

The present inventors have further studied and found that fatty acids hydroxylated at the 13-position, 10-position, the 15-position, the 12-position are produced, using a novel enzyme (FA-HY), respectively from an unsaturated fatty acid having 18 carbon atoms and a cis double bond at the 12-position (linoleic acid, γ-linolenic acid, α-linolenic acid, stearidonic acid etc.), unsaturated fatty acid having 16 carbon atoms and a cis double bond at the 9-position (pulmitoleic acid etc.), unsaturated fatty acid having 20 carbon atoms and a cis double bond at the 14-position (Dihomo-γ-linolenic acid or arachidonic acid etc.), unsaturated fatty acid having 18 or 20 carbon atoms and a cis double bond at the 11-position (cis-vaccenic acid, dihomo-γ-linolenic acid, mead acid etc.) as a substrate. Furthermore, they have found that 14-hydroxy-cis-4,cis-7,cis-10,cis-16,cis-19-docosapentaenoic acid is produced by using DHA as a substrate and 10-hydroxy-tetradecanoic acid is produced by using myristoleic acid as a substrate. In addition, they have found that some of the hydroxylated fatty acids in the obtained resultant products have a structure not found before and they are novel substances. They have found that such hydroxylated fatty acid containing a novel fatty acid has an activity as an agonist of nuclear receptor PPARα and PPARγ, and is a substances utilizable as a metabolism improving agent and the like.

They have also found that hydroxylated fatty acid obtained by the present invention as a starting material can be converted to oxo fatty acid by introducing an enzyme reaction or a chemical oxidation method using chromic acid. They have found a novel substance having a structure not found before among oxo fatty acids of such resultant products. They have found that such oxo fatty acid including a novel fatty acid has an activity as an agonist of nuclear receptors PPARα and PPARγ, and they are substances utilizable as a metabolism improving agent and the like. The present invention has been completed based on the above findings.

Accordingly, the present invention provides the following:

[1] An enzyme protein of any of the following (a)-(c):
(a) the enzyme protein consisting of the amino acid sequence shown in SEQ ID NO: 2,
(b) a protein comprising an amino acid sequence wherein one or plural amino acids in the amino acid sequence shown in SEQ ID NO: 2 are deleted and/or substituted and/or inserted and/or added, and having an enzyme activity that catalyzes a hydration reaction,
(c) a protein encoded by a base sequence that hybridizes to a nucleic acid consisting of a chain sequence complementary to the base sequence shown in SEQ ID NO: 1 under stringent conditions, and having an enzyme activity that catalyzes a hydration reaction;
[2] *Lactobacillus acidophilus* fungus or fungal debris thereof, comprising the enzyme protein of [1];
[3] a nucleic acid encoding the enzyme protein of [1];
[4] a vector comprising the nucleic acid of [3];
[5] a host cell transformed with the vector of [4];
[6] a method of producing the enzyme protein of [1], comprising culturing the host cell of [5] and recovering the enzyme from the culture;
[7] a method of producing a hydroxylated fatty acid having 18 carbon atoms and a hydroxyl group at the 13-position, comprising subjecting an unsaturated fatty acid having 18 carbon atoms and a cis double bond at the 12-position to a hydration reaction using the enzyme protein of [1];
[8] a method of producing an oxo fatty acid having 18 carbon atoms and a carbonyl group at the 13-position, comprising subjecting an unsaturated fatty acid having 18 carbon atoms and a cis double bond at the 12-position to a hydration reaction using the enzyme protein of [1] to induce a hydroxylated fatty acid having 18 carbon atoms and a hydroxyl group at the 13-position, and subjecting the hydroxylated fatty acid to a dehydrogenation reaction or chemical oxidation;
[9] a method of producing a hydroxylated fatty acid having 16 carbon atoms and a hydroxyl group at the 10-position, comprising subjecting an unsaturated fatty acid having 16 carbon atoms and a cis double bond at the 9-position to a hydration reaction using the enzyme protein of [1];
[10] a method of producing an oxo fatty acid having 16 carbon atoms and a carbonyl group at the 10-position, comprising subjecting an unsaturated fatty acid having 16 carbon atoms and a cis double bond at the 9-position to a hydration reaction using the enzyme protein of [1] to induce a hydroxylated fatty acid having 16 carbon atoms and a hydroxyl group at the 10-position, and subjecting the hydroxylated fatty acid to a dehydrogenation reaction or chemical oxidation;
[11] a method of producing a hydroxylated fatty acid having 20 carbon atoms and a hydroxyl group at the 15-position, comprising subjecting an unsaturated fatty acid having 20 carbon atoms and a cis double bond at the 14-position to a hydration reaction using the enzyme protein of [1];
[12] a method of producing an oxo fatty acid having 20 carbon atoms and a carbonyl group at the 15-position, comprising subjecting an unsaturated fatty acid having 20 carbon atoms and a cis double bond at the 14-position to a hydration reaction using the enzyme protein of [1] to induce a hydroxylated fatty acid having 20 carbon atoms and a hydroxy group at the 15-position, and subjecting the hydroxylated fatty acid to a dehydrogenation reaction or chemical oxidation;
[13] a method of producing a hydroxylated fatty acid having 18 or 20 carbon atoms and a hydroxyl group at the 12-position, comprising subjecting an unsaturated fatty acid having 18 or 20 carbon atoms and a cis double bond at the 11-position to a hydration reaction using the enzyme protein of [1];
[14] a method of producing an oxo fatty acid having 18 or 20 carbon atoms and a carbonyl group at the 12-position, comprising subjecting an unsaturated fatty acid having 18 or 20 carbon atoms and a cis double bond at the 11-position to a hydration reaction using the enzyme protein of [1] to induce a hydroxylated fatty acid having 18 or 20 carbon atoms and a hydroxyl group at the 12-position, and subjecting the hydroxylated fatty acid to a dehydrogenation reaction or chemical oxidation;
[15] the method of [7] or [8], wherein the unsaturated fatty acid having 18 carbon atoms and a cis double bond at the 12-position is linoleic acid, γ-linolenic acid, α-linolenic acid, stearidonic acid, 10-hydroxy-cis-12-octadecenoic acid, 10-hydroxy-cis-6,cis-12-octadecadienoic acid, 10-hydroxycis-12,cis-15-octadecadienoic acid, 10-hydroxy-cis-6,cis-12,cis-15-octadecatrienoic acid, 10-oxo-cis-12-octadecenoic acid, 10-oxo-cis-6,cis-12-octadecadienoic acid, 10-oxo-cis-12,cis-15-octadecadienoic acid, 10-oxo-cis-6,cis-12,cis-15-octadecatrienoic acid, pinolenic acid or columbinic acid;

[16] the method of [9] or [10], wherein the unsaturated fatty acid having 16 carbon atoms and a cis double bond at the 9-position is pulmitoleic acid;

[17] the method of [11] or [12], wherein the unsaturated fatty acid having 20 carbon atoms and a cis double bond at the 14-position is cis-11,cis-14-eicosadienoic acid, cis-11,cis-14,cis-17-eicosatrienoic acid, dihomo-γ-linolenic acid, cis-8,cis-11,cis-14,cis-17-eicosatetraenoic acid, arachidonic acid, sciadonic acid or juniperonic acid;

[18] the method of [13] or [14], wherein the unsaturated fatty acid having 18 or 20 carbon atoms and a cis double bond at the 11-position is cis-vaccenic acid, cis-11-cis-14-eicosadienoic acid, cis-11,cis-14,cis-17-eicosatrienoic, dihomo-γ-linolenic acid, mead acid, cis-8,cis-11,cis-14,cis-17-eicosatetraenoic acid or arachidonic acid;

[19] a method of producing 14-hydroxy-cis-4,cis-7,cis-10,cis-16,cis-19-docosapentaenoic acid, comprising subjecting cis-4,cis-7,cis-10,cis-13,cis-16,cis-19-docosahexaenoic acid to a hydration reaction using the enzyme protein of [1];

[20] a method of producing 14-oxo-cis-4,cis-7,cis-10,cis-16,cis-19-docosapentaenoic acid, comprising subjecting cis-4,cis-7,cis-10,cis-13,cis-16,cis-19-docosahexaenoic acid to a hydration reaction using the enzyme protein of [1] to induce 14-hydroxy-cis-4,cis-7,cis-10,cis-16,cis-19-docosapentaenoic acid, and subjecting the hydroxylated fatty acid to a dehydrogenation reaction or chemical oxidation;

[21] a method of producing 10-hydroxy-tetradecanoic acid, comprising subjecting cis-9-tetradecenoic acid (myristoleic acid) to a hydration reaction using the enzyme protein of [1];

[22] a method of producing 10-oxo-tetradecanoic acid, comprising subjecting cis-9-tetradecenoic acid (myristoleic acid) to a hydration reaction using the enzyme protein of [1] to induce 10-hydroxy-tetradecanoic acid, and subjecting the hydroxylated fatty acid to a dehydrogenation reaction or chemical oxidation;

[23] the method of [8], [10], [12], [14]-[18], [20] or [22], wherein the dehydrogenation reaction uses a dehydrogenase derived from Lactobacillus;

[24] the method of [23], wherein the Lactobacillus is Lactobacillus plantarum FERM BP-10549 strain;

[25] 13-hydroxy-cis-9,cis-15-octadecadienoic acid, 13-hydroxy-cis-6,cis-9,cis-15-octadecatrienoic acid, 10,13-dihydroxy-cis-6-octadecenoic acid, 10,13-dihydroxy-cis-15-octadecenoic acid, 10,13-dihydroxy-cis-6,cis-15-octadecadienoic acid, 10-oxo-13-hydroxy-cis-6-octadecenoic acid, 10-oxo-13-hydroxy-cis-15-octadecenoic acid, 10-oxo-13-hydroxy-cis-6,cis-15-octadecadienoic acid, 13-hydroxy-cis-5,cis-9-octadecadienoic acid or 13-hydroxy-trans-5,cis-9-octadecadienoic acid, which is produced by the method of [7];

[26] 15-hydroxy-cis-11,cis-17-eicosadienoic acid, 15-hydroxy-cis-8,cis-11-eicosadienoic acid, 15-hydroxy-cis-8,cis-11,cis-17-eicosatrienoic acid, 15-hydroxy-cis-5,cis-11-eicosadienoic acid or 15-hydroxy-cis-5,cis-11,cis-17-eicosatrienoic acid, which is produced by the method of [11];

[27] 12-hydroxy-cis-14-eicosenoic acid, 12-hydroxy-cis-14,cis-17-eicosadienoic acid or 12-hydroxy-cis-8,cis-14,cis-17-eicosatrienoic acid, which is produced by the method of [13];

[28] 13-oxo-cis-6,cis-9-octadecadienoic acid, 13-oxo-cis-6,cis-9,cis-15-octadecatrienoic acid, 10,13-dioxo-cis-6-octadecenoic acid, 10,13-dioxo-cis-15-octadecenoic acid, 10,13-dioxo-cis-6,cis-15-octadecadienoic acid, 13-oxo-cis-5,cis-9-octadecadienoic acid or 13-oxo-trans-5,cis-9-octadecadienoic acid, which is produced by the method of [8];

[29] 15-oxo-cis-11,cis-17-eicosadienoic acid, 15-oxo-cis-8,cis-11-eicosadienoic acid, 15-oxo-cis-8,cis-11,cis-17-eicosatrienoic acid, 15-oxo-cis-5,cis-11-eicosadienoic acid or 15-oxo-cis-5,cis-11,cis-17-eicosatrienoic acid, which is produced by the method of [12];

[30] 12-oxo-cis-14-eicosenoic acid, 12-oxo-cis-14,cis-17-eicosadienoic acid, 12-oxo-cis-8,cis-14-eicosadienoic acid, 12-oxo-cis-5,cis-8-eicosadienoic acid or 12-oxo-cis-8,cis-14,cis-17-eicosatrienoic acid, which is produced by the method of [14];

[31] 14-hydroxy-cis-4,cis-7,cis-10,cis-16,cis-19-docosapentaenoic acid produced by the method of [19];

[32] 14-oxo-cis-4,cis-7,cis-10,cis-16,cis-19-docosapentaenoic acid, which is produced by the method of [20];

[33] a fatty acid-containing substance comprising the hydroxylated fatty acid or oxo fatty acid of any one of [25]-[32];

[34] use of Lactobacillus acidophilus fungus or fungal debris thereof, comprising the enzyme protein of [1] in the production of the hydroxylated fatty acid or oxo fatty acid of any one of [25]-[32].

Effect of the Invention

In the present invention, a fatty acid hydration enzyme (FA-HY) conventionally not known was found, a method of converting unsaturated fatty acid having 16, 18 or 20 carbon atoms, DHA or myristoleic acid to a hydroxylated fatty acid was found, and further, a method of oxidizing a hydroxyl group of the resulting substance by an enzyme reaction or a chemical reaction was found. The rare fatty acid etc. to be produced are extremely useful since they are used in various fields such as medicament, food, cosmetic and the like. In addition, a novel rare fatty acid can be produced by the production using a novel enzyme, and the novel rare fatty acid also has an activity as an agonist of nuclear receptors PPARα and PPARγ. Therefore, it can be a useful substance in various fields such as medicament, food, cosmetic and the like.

DESCRIPTION OF EMBODIMENTS

Figure 1:
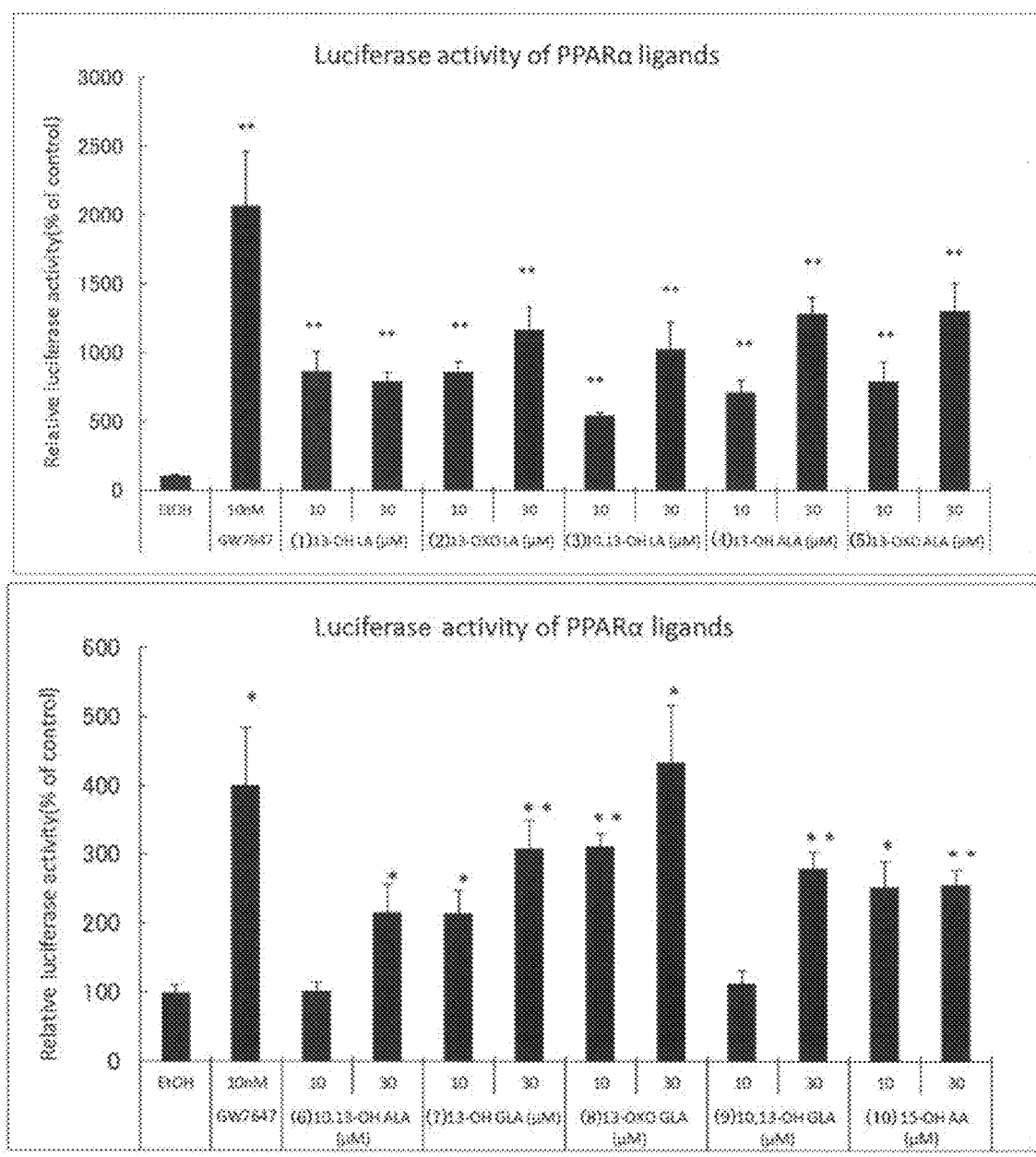
FIG. 1 shows the results of PPARα agonist activity of rare fatty acids derived from linoleic acid, α-linolenic acid, γ-linolenic acid, and arachidonic acid. EtOH shows a negative control (ethanol addition), and GW7647 shows a positive control (PPARα agonist addition). The vertical axis shows relative luciferase activity.

The present invention is explained in detail below.
the present invention provides a novel fatty acid hydration enzyme "FA-HY".

Specifically, the novel enzyme "FA-HY" of the present invention is
(a) the enzyme protein consisting of the amino acid sequence shown in SEQ ID NO: 2,
(b) a protein comprising an amino acid sequence wherein one or plural amino acids in the amino acid sequence shown in SEQ ID NO: 2 are deleted and/or substituted and/or inserted and/or added, and having an enzyme activity that the enzyme protein consisting of the amino acid sequence shown in SEQ ID NO: 2 has, or
(c) a protein encoded by a base sequence that hybridizes to a nucleic acid consisting of a chain sequence complementary to the base sequence shown in SEQ ID NO: 1 under stringent conditions, and having an enzyme activity that the enzyme protein consisting of the amino acid sequence shown in SEQ ID NO: 2 has.

More specific examples of the above-mentioned (b) include a protein containing (i) an amino acid sequence which is the amino acid sequence shown in SEQ ID NO: 2, wherein 1-20, preferably 1-10, more preferably 1-several (5, 4, 3 or 2) amino acids are deleted, (ii) an amino acid sequence which is the amino acid sequence shown in SEQ ID NO: 2, wherein 1-20, preferably 1-10, more preferably 1-several number (5, 4, 3 or 2) amino acids are added, (iii) an amino acid sequence which is the amino acid sequence shown in SEQ ID NO: 2, wherein 1-20, preferably 1-10, more preferably 1-several (5, 4, 3 or 2) amino acids are inserted, (iv) an amino acid sequence which is the amino acid sequence shown in SEQ ID NO: 2, wherein 1-20, preferably 1-10, more preferably 1-several (5, 4, 3 or 2) amino acids are substituted by other amino acids, or (v) an amino acid sequence obtained by combining them. When amino acids with similar properties (e.g., glycine and alanine, valine and leucine and isoleucine, serine and threonine, aspartic acid and glutamic acid, asparagine and glutamine, lysine and arginine, cysteine and methionine, phenylalanine and tyrosine etc.) are substituted with each other and the like, a greater number of substitutions and the like are possible.

When amino acids are deleted, substituted or inserted as mentioned above, the positions of deletion, substitution and insertion are not particularly limited as long as the above-mentioned enzyme activity is maintained.

In the above-mentioned (c), the "stringent conditions" are conditions under which nucleotide sequences having high identity, for example, identity of 70, 80, 90, 95 or 99% or above, hybridize to each other and nucleotide sequences having identity lower than that do not hybridize; specifically, conditions of washing once, more preferably 2-3 times, at the salt concentration and temperature corresponding to those in the washing conditions of general Southern hybridization (60° C., 1×SSC, 0.1% SDS, preferably, 0.1×SSC, 0.1% SDS, more preferably, 68° C., 0.1×SSC, 0.1% SDS) and the like.

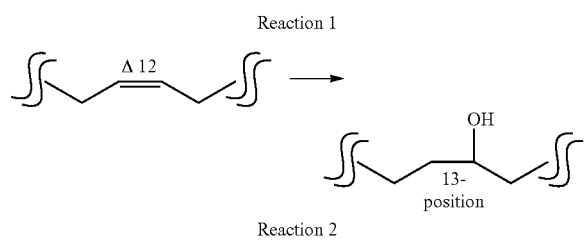

Reaction 1

Reaction 2

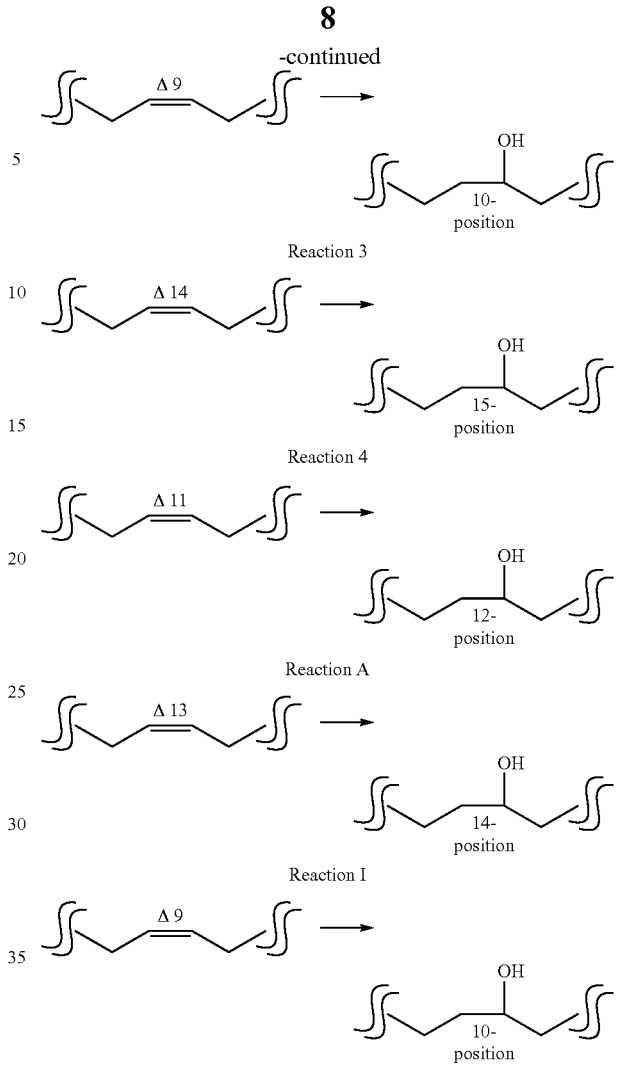

Reaction 3

Reaction 4

Reaction A

Reaction I

Regarding the above-mentioned (b) or (c), the enzyme activity that the enzyme protein consisting of the amino acid sequence shown in SEQ ID NO: 2 has is not particularly limited as long as it has at least one, preferably all, of (1) an enzyme activity capable of converting an unsaturated fatty acid having 18 carbon atoms and a cis double bond at the 12-position (hereinafter sometimes to be abbreviated as "cis-12 unsaturated fatty acid") utilized as a substrate to a hydroxylated fatty acid having 18 carbon atoms and a hydroxyl group at the 13-position (hereinafter sometimes to be abbreviated as "13-hydroxy fatty acid") (reaction 1), (2) an enzyme activity capable of converting an unsaturated fatty acid having 16 carbon atoms and a cis double bond at the 9-position (hereinafter sometimes to be abbreviated as "cis-9 unsaturated fatty acid")) utilized as a substrate to a hydroxylated fatty acid having 16 carbon atoms and a hydroxyl group at the 10-position (hereinafter sometimes to be abbreviated as "10-hydroxy fatty acid") (reaction 2), (3) an enzyme activity capable of converting an unsaturated fatty acid having 20 carbon atoms and a cis double bond at the 14-position (hereinafter sometimes to be abbreviated as "cis-14 unsaturated fatty acid")) utilized as a substrate to a hydroxylated fatty acid having 20 carbon atoms and a hydroxyl group at the 15-position (hereinafter sometimes to be abbreviated as "15-hydroxy fatty acid") (reaction 3), (4) an enzyme activity capable of converting an unsaturated fatty acid having 18 or 20 carbon atoms and a cis double bond at the 11-position (hereinafter sometimes to be abbreviated as "cis-11 unsaturated fatty acid")) utilized as a substrate to a hydroxylated fatty acid having 18 or 20 carbon atoms and a hydroxyl group at the 12-position (hereinafter sometimes to be abbreviated as "12-hydroxy fatty acid") (reaction 4), an enzyme activity capable of converting cis-4,cis-7,cis-10,cis-13,cis-16,cis-19-docosahexaenoic acid (DHA) to 14-hydroxy-cis-4,cis-7,cis-10,cis-16,cis-19-docosapentaenoic acid (reaction A), and an enzyme activity capable of converting cis-9-tetradecenoic acid (myristoleic acid) to 10-hydroxy-tetradecanoic acid (reaction I).

The above-mentioned "cis-12 unsaturated fatty acid", "cis-9 unsaturated fatty acid", "cis-14 unsaturated fatty acid", and "cis-11 unsaturated fatty acid" are not particularly limited as long as they are an unsaturated fatty acid having 18 carbon atoms and a cis double bond at the 12-position, an unsaturated fatty acid having 16 carbon atoms and a cis double bond at the 9-position, an unsaturated fatty acid having 20 carbon atoms and a cis double bond at the 14-position, an unsaturated fatty acid having 18 or 20 carbon atoms and a cis double bond at the 11-position, respectively and, for example, monovalent unsaturated fatty acid, divalent unsaturated fatty acid, trivalent unsaturated fatty acid, tetravalent unsaturated fatty acid, pentavalent unsaturated fatty acid and the like can be mentioned. In the present specification, the "fatty acid" encompasses not only free acids but also ester form, salt with basic compound and the like. The "DHA" and "myristoleic acid" also encompass not only free acids but also ester form, salt with basic compound and the like.

The FA-HY of the present invention can be isolated from, for example, the fungus, culture medium of *Lactobacillus acidophilus* by a protein separation and purification technique known per se. Alternatively, FA-HY may be used as the fungus of *Lactobacillus acidophilus* containing FA-HY or fungal debris thereof. The fungus of *Lactobacillus acidophilus* containing FA-HY is not particularly limited as long as it contains the FA-HY of the present invention and, for example, NITE BP-01788 and the like can be mentioned. Alternatively, FA-HY can also be produced as a recombinant protein by isolating a gene encoding FA-HY according to the method described in Example 2, subcloning same into a suitable vector, introducing same into a suitable host such as *Escherichia coli* and the like and culturing same. FA-HY may be a purified one or a crudely purified one. Alternatively, hydratase may be expressed in fungus such as *Escherichia coli* and the like and the fungus itself may be used or culture medium thereof may be used. Furthermore, the enzyme may be of a free form, or immobilized by various carriers.

As a vector containing a nucleic acid encoding FA-HY of the present invention, one suitable for a host cell to be introduced with the vector may be appropriately selected according to the object (e.g., protein expression) and can be used. In the case of an expression vector, it contains the nucleic acid of the present invention, which is operably linked to an appropriate promoter, and preferably contains a transcription termination signal, i.e., terminator region, at the downstream of the nucleic acid of the present invention. Furthermore, it can also contain a selection marker gene for selection of a transformant (drug resistance gene, gene that complements auxotrophic mutation etc.). Also, it may contain a sequence encoding a tag sequence useful for separation and purification of the expressed protein and the like. In addition, the vector may be incorporated into the genome of a target host cell. The vector of the present invention can be introduced into a target host cell by a transformation method known per se such as a competent cell method, a protoplast method, a calcium phosphate coprecipitation method and the like.

In the present invention, the "host cell" may be any cell as long as it can express a vector containing a nucleic acid encoding FA-HY of the present invention, and bacterium, yeast, fungi, higher eukaryotic cell and the like can be mentioned. Examples of the bacterium include gram-positive bacteria such as *bacillus, Streptomyces* and the like and gram negative bacteria such as *Escherichia coli* and the like. A recombinant cell introduced with a vector containing a nucleic acid encoding FA-HY can be cultivated by a method known per se which is suitable for the host cell.

"Purification" of the FA-HY of the present invention can be performed by a method known per se, for example, fungi collected by centrifugation and the like are ruptured by ultrasonication or glass beads and the like, solid such as cell debris is removed by centrifugation and the like, and the like to give a crude enzyme solution, which is subjected to a salting out method using ammonium sulfate, sodium sulfate and the like, chromatographys such as ion exchange chromatography, gel filtration chromatography, affinity chromatography and the like, gel electrophoresis and the like.

The FA-HY of the present invention has, as mentioned above, an enzyme activity capable of converting cis-12 unsaturated fatty acid, cis-9 unsaturated fatty acid, cis-14 unsaturated fatty acid, cis-11 unsaturated fatty acid, DHA, myristoleic acid utilized as substrates to 13-hydroxy fatty acid, 10-hydroxy fatty acid, 15-hydroxy fatty acid, 12-hydroxy fatty acid, 14-hydroxy-cis-4,cis-7,cis-10,cis-16,cis-19-docosapentaenoic acid, 10-hydroxy-tetradecanoic acid, respectively. Therefore, the present invention also provides [1] a method of producing 13-hydroxy fatty acid from cis-12 unsaturated fatty acid by a hydration reaction using the FA-HY of the present invention (production method 1), [2] a method of producing 10-hydroxy fatty acid from cis-9 unsaturated fatty acid by a hydration reaction using the FA-HY of the present invention (production method 2), [3] a method of producing 15-hydroxy fatty acid from cis-14 unsaturated fatty acid by a hydration reaction using the FA-HY of the present invention (production method 3), [4] a method of producing 12-hydroxy fatty acid from cis-11 unsaturated fatty acid by a hydration reaction using the FA-HY of the present invention (production method 4), [A] a method of producing 14-hydroxy-cis-4,cis-7,cis-10,cis-16, cis-19-docosapentaenoic acid from DHA by a hydration reaction using the FA-HY of the present invention (production method A), and [I] a method of producing 10-hydroxy-tetradecanoic acid from myristoleic acid by a hydration reaction using the FA-HY of the present invention (production method I).

Examples of the "cis-12 unsaturated fatty acid" in the production method 1 of the present invention include cis-9,cis-12-octadecadienoic acid (linoleic acid), cis-6,cis-9,cis-12-octadecatrienoic acid (γ-linolenic acid), cis-9,cis-12,cis-15-octadecatrienoic acid (α-linolenic acid), cis-6,cis-9,cis-12,cis-15-octadecatetraenoic acid (stearidonic acid), as well as 10-hydroxy-cis-12-octadecenoic acid, 10-hydroxy-cis-6, cis-12-octadecadienoic acid, 10-hydroxy-cis-12,cis-15-octadecadienoic acid, 10-hydroxy-cis-6,cis-12,cis-15-octadecatrienoic acid, 10-oxo-cis-12-octadecenoic acid, 10-oxo-cis-6,cis-12-octadecadienoic acid, 10-oxo-cis-12,cis-15-octadecadienoic acid, 10-oxo-cis-6,cis-12,cis-15-octadecatrienoic acid, cis-5,cis-9,cis-12-octadecatrienoic acid (pinolenic acid), trans-5,cis-9,cis-12-octadecatrienoic acid (columbinic acid), which are now producible by WO 2013/168310, and the like. These substrates may be obtained by a method other than WO 2013/168310.

Examples of the "13-hydroxy fatty acid" produced by production method 1 of the present invention include 13-hydroxy-cis-9-octadecenoic acid induced from cis-9,cis-12-octadecadienoic acid (linoleic acid), 13-hydroxy-cis-6,cis-9-octadecadienoic acid induced from cis-6,cis-9,cis-12-octadecatrienoic acid (γ-linolenic acid), 13-hydroxy-cis-9,cis-15-octadecadienoic acid induced from cis-9,cis-12,cis-15-octadecatrienoic acid (α-linolenic acid), 13-hydroxy-cis-6,cis-9,cis-15-octadecatrienoic acid induced from cis-6,cis-9,cis-12,cis-15-octadecatetraenoic acid (stearidonic acid), 10,13-dihydroxy-octadecanoic acid induced from 10-hydroxy-cis-12-octadecenoic acid, 10,13-dihydroxy-cis-6-octadecenoic acid induced from 10-hydroxy-cis-6,cis-12-octadecadienoic acid, 10,13-dihydroxy-cis-15-octadecenoic acid induced from 10-hydroxy-cis-12,cis-15-octadecadienoic acid, 10,13-dihydroxy-cis-6,cis-15-octadecadienoic acid induced from 10-hydroxy-cis-6,cis-12,cis-15-octadecatrienoic acid, 10-oxo-13-hydroxy-octadecanoic acid induced from 10-oxo-cis-12-octadecenoic acid, 10-oxo-13-hydroxy-cis-6-octadecenoic acid induced from 10-oxo-cis-6,cis-12-octadecadienoic acid, 10-oxo-13-hydroxy-cis-15-octadecenoic acid induced from 10-oxo-cis-12,cis-15-octadecadienoic acid, 10-oxo-13-hydroxy-cis-6,cis-15-octadecadienoic acid induced from 10-oxo-cis-6,cis-12,cis-15-octadecatrienoic acid, 13-hydroxy-cis-5,cis-9-octadecadienoic acid induced from cis-5,cis-9,cis-12-octadecatrienoic acid (pinolenic acid), 13-hydroxy-trans-5,cis-9-octadecadienoic acid induced from trans-5,cis-9,cis-12-octadecatrienoic acid (columbinic acid) and the like.

Examples of the "cis-9 unsaturated fatty acid" in production method 2 of the present invention include cis-9-hexadecenoic acid (pulmitoleic acid) and the like.

Examples of the "10-hydroxy fatty acid" produced by production method 2 of the present invention include 10-hydroxy-hexadecanoic acid induced from cis-9-hexadecenoic acid (pulmitoleic acid) and the like.

Examples of the "cis-14 unsaturated fatty acid" in production method 3 of the present invention include cis-11,cis-14-eicosadienoic acid, cis-11,cis-14,cis-17-eicosatrienoic acid, cis-8,cis-11,cis-14-eicosatrienoic acid (dihomo-γ-linolenic acid), cis-8,cis-11,cis-14,cis-17-eicosatetraenoic acid, cis-5,cis-8,cis-11,cis-14-eicosatetraenoic acid (arachidonic acid), cis-5,cis-11,cis-14-eicosatrienoic acid (sciadonic acid), cis-5,cis-11,cis-14,cis-17-eicosatetraenoic acid (juniperonic acid) and the like.

Examples of the "15-hydroxy fatty acid" produced by production method 3 of the present invention include 15-hydroxy-cis-11-eicosenoic acid induced from cis-11,cis-14-eicosadienoic acid, 15-hydroxy-cis-11,cis-17-eicosadienoic acid induced from cis-11,cis-14,cis-17-eicosatrienoic acid, 15-hydroxy-cis-8,cis-11-eicosadienoic acid induced from cis-8,cis-11,cis-14-eicosatrienoic acid (dihomo-γ-linolenic acid), 15-hydroxy-cis-8,cis-11,cis-17-eicosatrienoic acid induced from cis-8,cis-11,cis-14,cis-17-eicosatetraenoic acid, 15-hydroxy-cis-5,cis-8,cis-11-eicosatrienoic acid induced from cis-5,cis-8,cis-11,cis-14-eicosatetraenoic acid (arachidonic acid), 15-hydroxy-cis-5,cis-11-eicosadienoic acid induced from cis-5,cis-11,cis-14-eicosatrienoic acid (sciadonic acid), 15-hydroxy-cis-5,cis-11,cis-17-eicosatrienoic acid induced from cis-5,cis-11,cis-14,cis-17-eicosatetraenoic acid (juniperonic acid) and the like.

Examples of the "cis-11 unsaturated fatty acid" in production method 4 of the present invention include cis-11-octadecenoic acid (cis-vaccenic acid), cis-11,cis-14-eicosadienoic acid, cis-11,cis-14,cis-17-eicosatrienoic acid, cis-8,cis-11,cis-14-eicosatrienoic acid (dihomo-γ-linolenic acid), cis-5,cis-8,cis-11-eicosatrienoic acid (mead acid), cis-8,cis-11,cis-14,cis-17-eicosatetraenoic acid, cis-5,cis-8,cis-11,cis-14-eicosatetraenoic acid (arachidonic acid) and the like.

Examples of the "12-hydroxy fatty acid" produced by production method 4 of the present invention include 12-hydroxy-octadecanoic acid induced from cis-11-octadecenoic acid (cis-vaccenic acid), 12-hydroxy-cis-14-eicosenoic acid induced from cis-11,cis-14-eicosadienoic acid, 12-hydroxy-cis-14,cis-17-eicosadienoic acid induced from cis-11,cis-14,cis-17-eicosatrienoic acid, 12-hydroxy-cis-8,cis-14-eicosadienoic acid induced from cis-8,cis-11,cis-14-eicosatrienoic acid (dihomo-γ-linolenic acid), 12-hydroxy-cis-5,cis-8-eicosadienoic acid induced from cis-5,cis-8,cis-11-eicosatrienoic acid (mead acid), 12-hydroxy-cis-8,cis-14,cis-17-eicosatrienoic acid induced from cis-8,cis-11,cis-14,cis-17-eicosatetraenoic acid, 12-hydroxy-cis-5,cis-8,cis-14-eicosatrienoic acid induced from cis-5,cis-8,cis-11,cis-14-eicosatetraenoic acid (arachidonic acid) and the like.

The hydration reaction may be performed in a suitable buffer (e.g., phosphate buffer, tris buffer, borate buffer etc.) by mixing unsaturated fatty acid, which is a substrate, and FA-HY of the present invention at suitable concentrations and incubating the mixture. The substrate concentration is, for example, 1-1000 g/L, preferably 10-500 g/L, more preferably 20-250 g/L. The amount of the aforementioned FA-HY to be added is, for example, 0.001-10 mg/mL, preferably 0.1-5 mg/mL, more preferably 0.2-2 mg/mL.

A "cofactor" may be used for a hydration reaction (reaction 1-4, reaction A or reaction I) and, for example, FAD and the like can be used. The concentration of addition may be any as long as the hydration reaction proceeds efficiently. It is preferably 0.001-20 mM, more preferably 0.01-10 mM.

Furthermore, an "activator" may be used for the hydration reaction and, for example, 1 or 2 compounds selected from the group consisting of NADH and NADPH can be mentioned. The concentration of addition thereof may be any as long as the hydration reaction proceeds efficiently. It is preferably 0.1-20 mM, more preferably 1-10 mM.

The hydration reaction is desirably performed at a preferable temperature and in a preferable pH range for the FA-HY of the present invention. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one preferable embodiment of the present invention, the FA-HY of the present invention is provided to the reaction system in the form of recombinant cells (e.g., *Escherichia coli, Bacillus subtilis*, yeast, insect cell, animal cell etc.) introduced with an expression vector containing a nucleic acid encoding same. In this case, the hydration reaction can also be performed by cultivating the cells in a liquid medium suitable for the culture of the cells and added with cofactor and a substrate and, where necessary, an activator.

Reaction 5

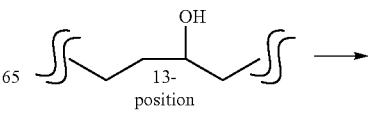

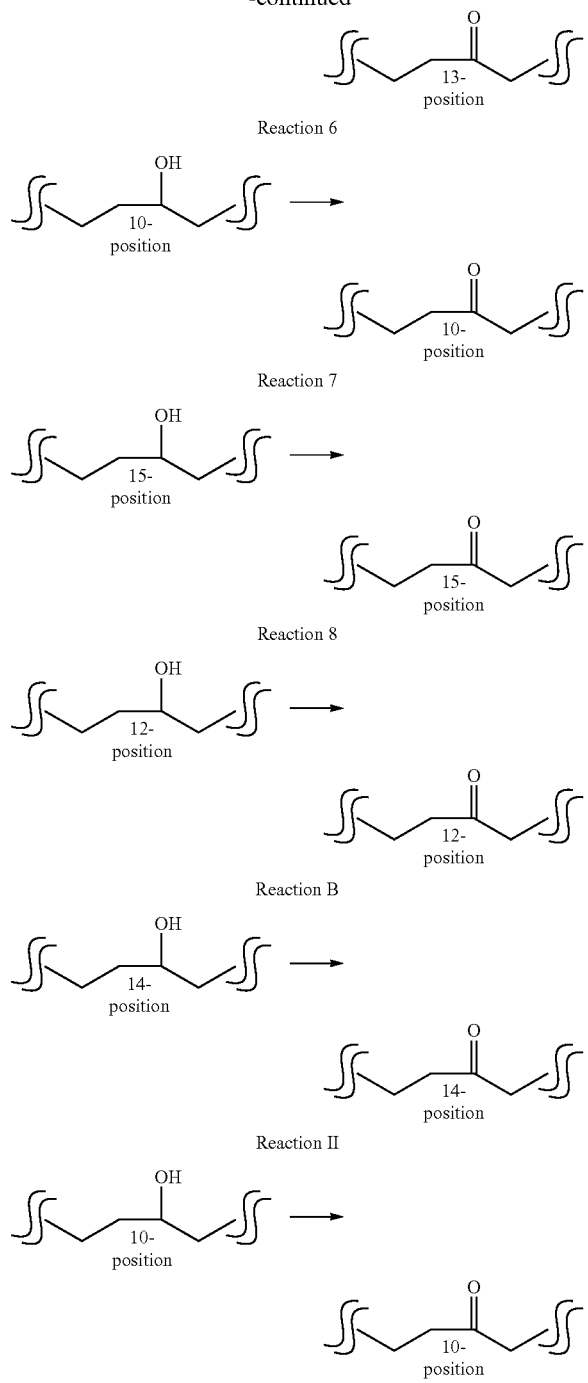

Reaction 6

Reaction 7

Reaction 8

Reaction B

Reaction II

Furthermore, by a dehydrogenation reaction or chemical oxidation using chrome acid, an oxo fatty acid having 18 carbon atoms and a carbonyl group at the 13-position (hereinafter sometimes to be abbreviated as "13-oxo fatty acid") is produced from 13-hydroxy fatty acid obtained in production methods 1-4, production method A, production method I of the present invention (reaction 5), an oxo fatty acid having 16 carbon atoms and a carbonyl group at the 10-position (hereinafter sometimes to be abbreviated as "10-oxo fatty acid") is produced from 10-hydroxy fatty acid (reaction 6), an oxo fatty acid having 20 carbon atoms and a carbonyl group at the 15-position (hereinafter sometimes to be abbreviated as "15-oxo fatty acid") is produced from 15-hydroxy fatty acid (reaction 7), an oxo fatty acid having 18 or 20 carbon atoms and a carbonyl group at the 12-position (hereinafter sometimes to be abbreviated as "12-oxo fatty acid") is produced from 12-hydroxy fatty acid (reaction 8), 14-oxo-cis-4,cis-7,cis-10,cis-16,cis-19-docosapentaenoic acid is produced from 14-hydroxy-cis-4,cis-7,cis-10,cis-16,cis-19-docosapentaenoic acid (reaction B), and 10-oxo-tetradecanoic acid is produced from 10-hydroxy-tetradecanoic acid (reaction II).

Therefore, the present invention also provides [5] a method of producing 13-oxo fatty acid, comprising subjecting cis-12 unsaturated fatty acid to a hydration reaction using the FA-HY of the present invention to induce 13-hydroxy fatty acid, and subjecting the 13-hydroxy fatty acid to a dehydrogenation reaction or chemical oxidation (production method 5), [6] a method of producing 10-oxo fatty acid, comprising subjecting cis-9 unsaturated fatty acid to a hydration reaction using the FA-HY of the present invention to induce 10-hydroxy fatty acid, and subjecting the 10-hydroxy fatty acid to a dehydrogenation reaction or chemical oxidation (production method 6), [7] a method of producing 15-oxo fatty acid, comprising subjecting cis-14 unsaturated fatty acid to a hydration reaction using the FA-HY of the present invention to induce 15-hydroxy fatty acid, and subjecting the 15-hydroxy fatty acid to a dehydrogenation reaction or chemical oxidation (production method 7), [8] a method of producing 12-oxo fatty acid, comprising subjecting cis-11 unsaturated fatty acid to a hydration reaction using the FA-HY of the present invention to induce 12-hydroxy fatty acid, and subjecting the 12-hydroxy fatty acid to a dehydrogenation reaction or chemical oxidation (production method 8), [B] a method of producing 14-oxo-cis-4,cis-7,cis-10,cis-16,cis-19-docosapentaenoic acid, comprising subjecting DHA to a hydration reaction using the FA-HY of the present invention to induce 14-hydroxy-cis-4,cis-7,cis-10,cis-16,cis-19-docosapentaenoic acid, and subjecting the 14-hydroxy-cis-4,cis-7,cis-10,cis-16,cis-19-docosapentaenoic acid to a dehydrogenation reaction or chemical oxidation (production method B), and [II] a method of producing 10-oxo-tetradecanoic acid, comprising subjecting myristoleic acid to a hydration reaction using the FA-HY of the present invention to induce 10-hydroxy-tetradecanoic acid, and subjecting the 10-hydroxy-tetradecanoic acid to a dehydrogenation reaction or chemical oxidation (production method II).

The "cis-12 unsaturated fatty acid", "cis-9 unsaturated fatty acid", "cis-14 unsaturated fatty acid", "cis-11 unsaturated fatty acid" in the production methods 5-8 of the present invention are the same as the substrates in the above-mentioned production methods 1-4.

Examples of the "13-oxo fatty acid" produced by the production method 5 of the present invention include 13-oxo-cis-9-octadecenoic acid induced from cis-9,cis-12-octadecadienoic acid (linoleic acid), 13-oxo-cis-6,cis-9-octadecadienoic acid induced from cis-6,cis-9,cis-12-octadecatrienoic acid (γ-linolenic acid), 13-oxo-cis-9,cis-15-octadecadienoic acid induced from cis-9,cis-12,cis-15-octadecatrienoic acid (α-linolenic acid), 13-oxo-cis-6,cis-9,cis-15-octadecatrienoic acid induced from cis-6,cis-9,cis-12,cis-15-octadecatetraenoic acid (stearidonic acid), 10,13-dioxo-octadecanoic acid induced from 10-hydroxy-cis-12-octadecenoic acid or 10-oxo-cis-12-octadecenoic acid, 10,13-dioxo-cis-6-octadecenoic acid induced from 10-hydroxy-cis-6,cis-12-octadecadienoic acid or 10-oxo-cis-6,cis-12-octadecadienoic acid, 10,13-dioxo-cis-15-octadecenoic acid induced from 10-hydroxy-cis-12,cis-15-octadecadienoic acid or 10-oxo-cis-12,cis-15-octadecadienoic acid, 10,13-dioxo-cis-6,cis-15-octadecadienoic acid induced from 10-hydroxy-cis-6,cis-12,cis-15-octadecatrienoic acid or 10-oxo-cis-6,cis-12,cis-15-octadecatrienoic acid, 13-oxo-cis-5,cis-9-octadecadienoic acid induced from cis-5,cis-9,cis-12-octadecatrienoic acid (pinolenic acid), 13-oxo-trans-5,cis-9-octadecadienoic acid induced from trans-5,cis-9,cis-12-octadecatrienoic acid (columbinic acid) and the like.

Examples of the "10-oxo fatty acid" produced by the production method 6 of the present invention include 10-oxo-hexadecanoic acid induced from cis-9-hexadecenoic acid (pulmitoleic acid) and the like.

Examples of the "15-oxo fatty acid" produced by the production method 7 of the present invention include 15-oxo-cis-11-eicosenoic acid induced from cis-11,cis-14-eicosadienoic acid, 15-oxo-cis-11,cis-17-eicosadienoic acid induced from cis-11,cis-14,cis-17-eicosatrienoic acid, 15-oxo-cis-8,cis-11-eicosadienoic acid induced from cis-8,cis-11,cis-14-eicosatrienoic acid (dihomo-γ-linolenic acid), 15-oxo-cis-8,cis-11,cis-17-eicosatrienoic acid induced from cis-8,cis-11,cis-14,cis-17-eicosatetraenoic acid, 15-oxo-cis-5,cis-8,cis-11-eicosatrienoic acid induced from cis-5,cis-8,cis-11,cis-14-eicosatetraenoic acid (arachidonic acid), 15-oxo-cis-5,cis-11-eicosadienoic acid induced from cis-5,cis-11,cis-14-eicosatrienoic acid (sciadonic acid), 15-oxo-cis-5,cis-11,cis-17-eicosatrienoic acid induced from cis-5,cis-11,cis-14,cis-17-eicosatetraenoic acid (juniperonic acid) and the like.

Examples of the "12-oxo fatty acid" produced by the production method 8 of the present invention include 12-oxo-octadecanoic acid induced from cis-11-octadecenoic acid (cis-vaccenic acid), 12-oxo-cis-14-eicosenoic acid induced from cis-11,cis-14-eicosadienoic acid, 12-oxo-cis-14,cis-17-eicosadienoic acid induced from cis-11,cis-14,cis-17-eicosatrienoic acid, 12-oxo-cis-8,cis-14-eicosadienoic acid induced from cis-8,cis-11,cis-14-eicosatrienoic acid (dihomo-γ-linolenic acid), 12-oxo-cis-5,cis-8-eicosadienoic acid induced from cis-5,cis-8,cis-11-eicosatrienoic acid (mead acid), 12-oxo-cis-8,cis-14,cis-17-eicosatrienoic acid induced from cis-8,cis-11,cis-14,cis-17-eicosatetraenoic acid, 12-oxo-cis-5,cis-8,cis-14-eicosatrienoic acid induced from cis-5,cis-8,cis-11,cis-14-eicosatetraenoic acid (arachidonic acid) and the like.

The dehydrogenase to be used in the production methods 5-8, production method B or production method II of the present invention is not particularly limited as long as it is an enzyme capable of converting 13-hydroxy fatty acid, 10-hydroxy fatty acid, 15-hydroxy fatty acid, 12-hydroxy fatty acid, 14-hydroxy-cis-4,cis-7,cis-10,cis-16,cis-19-docosapentaenoic acid, 10-hydroxy-tetradecanoic acid utilized as substrates to 13-oxo fatty acid, 10-oxo fatty acid, 15-oxo fatty acid, 12-oxo fatty acid, 14-oxo-cis-4,cis-7,cis-10,cis-16,cis-19-docosapentaenoic acid, 10-oxo-tetradecanoic acid, respectively and, for example, Lactobacillus-derived hydroxylated fatty acid-dehydrogenase (CLA-DH) is preferable. More preferred is Lactobacillus plantarum-derived CLA-DH, and particularly preferred is L. plantarum FERM BP-10549 strain-derived CLA-DH. CLA-DH can be obtained by the method described in JP-A-2007-259712, the method described in WO 2013/168310. Dehydrogenase may be a purified one or a crudely purified one. Alternatively, dehydrogenase may be expressed in fungus such as Escherichia coli and the like and the fungus itself may be used or culture medium thereof may be used. Furthermore, the enzyme may be of a free form, or immobilized by various carriers.

The dehydrogenation reaction is performed in a suitable buffer (e.g., phosphate buffer, tris buffer, borate buffer etc.) by mixing 13-hydroxy fatty acid, 10-hydroxy fatty acid, 15-hydroxy fatty acid, 12-hydroxy fatty acid, 14-hydroxy-cis-4,cis-7,cis-10,cis-16,cis-19-docosapentaenoic acid, 10-hydroxy-tetradecanoic acid as substrates and dehydrogenase at suitable concentrations and incubating the mixture. The substrate concentration is, for example, 0.01-100 g/L, preferably 0.05-50 g/L, more preferably 0.1-5 g/L. The amount of dehydrogenase to be added is, for example, 0.001-10 mg/mL, preferably 0.005-1 mg/mL, more preferably 0.05-0.2 mg/mL.

A "cofactor" may be used for the dehydrogenation reaction and, for example, $NAD^+$, $NADP^+$ and the like can be used. The concentration of addition thereof may be any as long as the hydration reaction proceeds efficiently. It is preferably 0.001-20 mM, more preferably 0.01-10 mM.

The dehydrogenation reaction is desirably performed within the ranges of preferable temperature and preferable pH of dehydrogenase. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one embodiment of the present invention, dehydrogenase is subjected to the reaction system in the form of recombinant cells (e.g., Escherichia coli, Bacillus subtilis, yeast, insect cell, animal cell etc.) introduced with an expression vector containing a nucleic acid encoding same. In this case, the oxidation reaction can also be performed by cultivating the cells in a liquid medium suitable for the culture of the cells and added with a substrate and, where necessary, a cofactor and an activator.

In addition, by replacing the dehydrogenation reaction with a chemical oxidation using chromic acid, an oxo fatty acid similar to that by enzyme reaction can be chemically obtained.

As the chemical oxidation, methods known per se, for example, chromic acid oxidation, preferably Jones oxidation and the like can be mentioned. As the chromic acid, salts or complexes of the compound such as anhydrous chromic acid $CrO_3$, chromic acid $H_2CrO_4$ and dichromic acid $H_2Cr_2O_7$ can be used.

To be specific, sulfuric acid (2.3 ml) and water (7.7 ml) are added to anhydrous chromic acid (2.67 g), and acetone (90 ml) is added to the mixture to give a chromic acid solution. 2 g of hydroxylated fatty acid and 40 ml of acetone are added in an Erlenmeyer flask, and the above-mentioned chromic acid solution is added by one drop while stirring in a stirrer on ice. When the solution turns from blue to tea green, dropwise addition of the chromic acid solution is stopped, and the reaction is discontinued with isopropyl alcohol. The precipitated sediment is filtered through filter paper, placed in a separating funnel, diethyl ether (150 ml) and Milli-Q water (300 ml) are added, the mixture is shaken well, and the diethyl ether layer is washed several times with Milli-Q water. To the diethyl ether layer after washing is added an appropriate amount of sodium sulfate (anhydrous), the mixture is stirred and the residual water is removed. The anhydrous sodium sulfate added is filtered off through filter paper, the obtained diethyl ether layer is concentrated by a rotary evaporator, and the reaction product (oxo fatty acid) and unreacted substrate are extracted.

An extract obtained by an oxidation reaction with anhydrous chromic acid (mixture containing substrate and resultant product (oxo fatty acid)) is subjected to moderate-pressure chromatography, a solution that comes out from the column is recovered in fractions. The recovered each fraction is analyzed by LC/MS and gas chromatography, fractions containing oxo fatty acid alone are collected and concentrated by a rotary evaporator. A part of the obtained final resultant product is methylesterified, the purity of oxo fatty acid is evaluated by gas chromatography, and oxo fatty acid having a purity of not less than 98% can be obtained.

The following hydroxylated fatty acid and oxo fatty acid obtained by the production methods 1-8 and production methods A, B of the present invention are novel fatty acids having structures conventionally not known.

<Hydroxylated Fatty Acid>
13-hydroxy-cis-9,cis-15-octadecadienoic acid
13-hydroxy-cis-6,cis-9,cis-15-octadecatrienoic acid
13-hydroxy-cis-5,cis-9-octadecadienoic acid
13-hydroxy-trans-5,cis-9-octadecadienoic acid
12-hydroxy-cis-14-eicosenoic acid
12-hydroxy-cis-14,cis-17-eicosadienoic acid
15-hydroxy-cis-11,cis-17-eicosadienoic acid
15-hydroxy-cis-8,cis-11-eicosadienoic acid
12-hydroxy-cis-8,cis-14,cis-17-eicosatrienoic acid
15-hydroxy-cis-8,cis-11,cis-17-eicosatrienoic acid
15-hydroxy-cis-5,cis-11-eicosadienoic acid
15-hydroxy-cis-5,cis-11,cis-17-eicosatrienoic acid
10,13-dihydroxy-cis-6-octadecenoic acid
10,13-dihydroxy-cis-15-octadecenoic acid
10,13-dihydroxy-cis-6,cis-15-octadecadienoic acid
10-oxo-13-hydroxy-cis-6-octadecenoic acid
10-oxo-13-hydroxy-cis-15-octadecenoic acid
10-oxo-13-hydroxy-cis-6,cis-15-octadecadienoic acid
14-hydroxy-cis-4,cis-7,cis-10,cis-16,cis-19-docosapentaenoic acid <Oxo Fatty Acid>
13-oxo-cis-6,cis-9-octadecadienoic acid
13-oxo-cis-6,cis-9,cis-15-octadecatrienoic acid
13-oxo-cis-5,cis-9-octadecadienoic acid
13-oxo-trans-5,cis-9-octadecadienoic acid
12-oxo-cis-14-eicosenoic acid
12-oxo-cis-14,cis-17-eicosadienoic acid
15-oxo-cis-11,cis-17-eicosadienoic acid
15-oxo-cis-8,cis-11-eicosadienoic acid
12-oxo-cis-8,cis-14-eicosadienoic acid
12-oxo-cis-5,cis-8-eicosadienoic acid
12-oxo-cis-8,cis-14,cis-17-eicosatrienoic acid
15-oxo-cis-8,cis-11,cis-17-eicosatrienoic acid
15-oxo-cis-5,cis-11-eicosadienoic acid
15-oxo-cis-5,cis-11,cis-17-eicosatrienoic acid
10,13-dioxo-cis-6-octadecenoic acid
10,13-dioxo-cis-15-octadecenoic acid
10,13-dioxo-cis-6,cis-15-octadecadienoic acid
14-oxo-cis-4,cis-7,cis-10,cis-16,cis-19-docosapentaenoic acid Since the hydroxylated fatty acids and oxo fatty acids obtained by the present invention have an activity as an agonist of nuclear receptors PPARα and PPARγ, they can be utilized as metabolism improving agents and the like. Therefore, novel hydroxylated fatty acids and oxo fatty acids are also novel substances that can be utilized as metabolism improving agents and the like.

The hydroxylated fatty acid and oxo fatty acid obtained in the present invention can be used by being blended with, for example, medicament, food or cosmetic agent based on the conventionally-known physiological activity.

The dosage form of the medicaments containing hydroxylated fatty acid, oxo fatty acid includes, for example, powder, granule, pill, soft capsule, hard capsules, tablet, chewable tablet, quick-integrating tablet, syrup, liquid, suspension, suppository, ointment, cream, gel, adhesive, inhalant, injection and the like. A preparation thereof is formulated according to a conventional method. Since oxo fatty acid and the like are poorly soluble in water, they are dissolved in a non-hydrophilic organic solvent such as plant-derived oil, animal-derived oil and the like or dispersed or emulsified in an aqueous solution together with an emulsifier, a dispersing agent, a surfactant and the like by a homogenizer (high-pressure homogenizer) and used.

Examples of the additives that can be used for formulating include animal and plant oils such as soybean oil, safflower oil, olive oil, germ oil, sunflower oil, beef fat, sardine oil and the like, polyalcohols such as polyethylene glycol, propylene glycol, glycerol, sorbitol and the like, surfactants such as sorbitan ester of fatty acid, sucrose ester of fatty acid, glycerin fatty acid ester, polyglycerol ester of fatty acid and the like, excipients such as purified water, lactose, starch, crystalline cellulose, D-mannitol, lecithin, gum arabic, sorbitol solution, carbohydrate solution and the like, sweetener, colorant, pH adjuster, flavor and the like. A liquid preparation may be dissolved or suspended in water or other suitable medium when in use. Also, tablet and granules may be coated by a well-known method.

For administration in the form of an injection, intravenous, intraperitoneal, intramuscular, subcutaneous, transdermal, intraarticular, intrasynovial, intrathecal, intraperiosteum, sublingual, oral administrations and the like are preferable, and intravenous administration or intraperitoneal administration is particularly preferable. The intravenous administration may be any of drip administration and bolus administration.

Examples of the form of the "food" containing the hydroxylated fatty acid, oxo fatty acid and the like obtained by the present invention include supplement (powder, granule, soft capsule, hard capsules, tablet, chewable tablet, quick-integrating tablet, syrup, liquid etc.), drinks (tea drinks, carbonic acid drinks, lactic acid drinks, sport drinks etc.), confectionery (gummy candy, jelly, gum, chocolate, cookie, candy etc.), oil, fat and oil foods (mayonnaise, dressing, butter, cream, margarine etc.) and the like.

The above-mentioned foods can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, *Agaricus* and the like.

Examples of the "cosmetics" containing the hydroxylated fatty acid, oxo fatty acid and the like obtained by the present invention include cream, skin milk, toner, microemulsion essence, bathing powder and the like, and flavor and the like may be added.

The present invention is explained in more detail in the following by referring to Examples. The Examples are mere exemplifications of the present invention and do not limit the scope of the present invention in any manner.

Example 1

Culture Method of *Lactobacillus acidophilus*

*Lactobacillus acidophilus* was inoculated in 15 ml of MRS liquid medium (manufactured by Difco; pH 6.5) from MRS high layer medium containing 2% agar and preserved at 4° C., and cultured at 37° C. for 20 hr. After the culture, the cells were collected by centrifugation at 3,000 rpm, 4° C. for 10 min to give the fungus of *Lactobacillus acidophilus*.

The aforementioned *Lactobacillus acidophilus* was deposited on Jan. 17, 2014 at the NITE Patent Microorganisms Depositary (NPMD) under deposit number NITE BP-01788.

Example 2

Cloning of gene of enzyme (FA-HY: fatty acid hydration enzyme) having the amino acid sequence shown in SEQ ID NO: 2

(1) Obtainment of Genome DNA

The aforementioned *Lactobacillus acidophilus* was inoculated in 10 ml of MRS liquid medium (manufactured by Difco) and standing culture was performed at 37° C. overnight, and the cells were collected by centrifugation. The obtained fungus was washed twice with 1 ml of sterile water and added with 0.1 ml of sterile water, 0.125 ml of lysis buffer (80 mM EDTA containing 200 mM Tris-HCl buffer (pH 8.0)), 0.25 ml of TE saturated phenol, and the mixture was vortexed for 1 min and the supernatant was recovered by centrifugation. To the obtained supernatant (0.2 ml) was added 0.2 ml of PCI solution (manufactured by Nacalai Tesque), and the mixture was hand-shaken, and the supernatant (0.125 ml) was recovered by centrifugation at 15,000 rpm, 4° C., 5 min. 0.0125 ml of 5 M NaCl, 0.31 ml of ethanol were added, and the mixture was stood at room temperature for 10 min and centrifuged at 15,000 rpm, 4° C., for 5 min. The supernatant was discarded and the pellets were washed with 0.2 ml of 70% ethanol. 0.1 ml of sterile water was added to the pellets and the mixture was incubated at 65° C. for 10 min to give genomic DNA.

(2) Obtainment of FA-HY Gene by PCR

In the published total genomic gene sequence of *Lactobacillus acidophilus* strain, open-reading-frame (ORF) having homology (about 32%) with gene sequence of CLA-HY in WO/2013/168310 was targeted. A sense primer (SEQ ID NO: 3) was designed based on the sequence of the 5' side of the initiation codon of ORF, and an antisense primer (SEQ ID NO: 4) was designed based on the sequence of the 3' side of the stop codon. Using these primers, genome DNA of *Lactobacillus acidophilus* as a templates, PCR was performed. The base sequence of about 1.8 kbp gene segment amplified as a result of PCR was analyzed. It was clarified that this gene segment contained a 1,773 bp one open-reading-frame (ORF) (SEQ ID NO: 1) starting from the initiation codon ATG and ending at stop codon TAG, and this gene was taken as FA-HY gene. The FA-HY gene encodes a protein consisting of 590 residual amino acids shown in SEQ ID NO: 2.

Example 3

Expression of (FA-HY) in *Escherichia coli*

A host vector system consisting of *Escherichia coli* expression vector pET21b (Novagen) and Rosetta 2 (DE3) strain was used. FA-HY gene segment amplified by PCR using genomic DNA of *Lactobacillus acidophilus* as a template was inserted into pET21b to construct an expression vector (pFA-HY). Rosetta 2 (DE3) strain was transformed with pFA-HY to give a transformed Rosetta/pFA-HY strain. The obtained Rosetta/pFA-HY strain was aerobically cultured at 37° C., 300 rpm in a 10 ml LB medium containing 0.5 mg ampicillin, 0.3 mg chloramphenicol (medium containing 1% Bacto Tripton (Difco), 0.5% yeast extract, 1% sodium chloride (pH 7.0)), 1 µl of 1 M IPTG was added when OD600 nm was 0.5, and the mixture was further cultured at 16° C. for 18 hr. After culture, the mixture was centrifuged at 3,000 rpm for 10 min to give wet fungus of Rosetta/pFA-HY strain.

Example 4

Production of Hydroxylated Fatty Acid from Unsaturated Fatty Acid Using Transformed *Escherichia coli* Expressing Fatty Acid Hydration Enzyme Hydroxylated fatty acid production test from various unsaturated fatty acids was performed using fatty acid hydration enzyme induction transformed *Escherichia coli*. The total amount of the reaction mixture was adjusted to 1 ml with 100 mM potassium phosphate buffer (pH 6.5) containing fatty acid hydration enzyme induction transformed *Escherichia coli* (wet body weight 0.3 g/ml), NADH (5 mM), FAD (0.1 mM), unsaturated fatty acid (100 mg), BSA (10 mg). The reaction was performed by anaerobically shaking at 37° C., 120 rpm for 16 to 60 hr in the presence of an oxygen adsorbent Anaeropack (Mitsubishi Chemical Corporation). After the reaction, 2 ml of chloroform, 2 ml of methanol, and 1 ml of 0.5% KCl were added to the reaction mixture (1 ml), and the mixture was stirred and the chloroform layer was recovered. The recovered chloroform layer was concentrated by a centrifugation evaporator, and the reaction product and unreacted substrate were extracted. A part of the extract was methylesterified and the reaction product was evaluated by gas chromatography.

Example 5

Purification of Resultant Product from Extract Obtained in Example 4 (Mixture Containing Substrate and Resultant Product (Hydroxylated Fatty Acid))

An extract obtained from Example 4 (mixture containing substrate and resultant product (hydroxylated fatty acid)) was subjected to moderate-pressure chromatography, a solution that came out from the column was recovered in fractions. The recovered each fraction was analyzed by LC/MS and gas chromatography, fractions containing resultant product (hydroxylated fatty acid) alone were collected and concentrated by a rotary evaporator. A part of the obtained final resultant product (hydroxylated fatty acid) was methylesterified, and the purity of the resultant product was evaluated by gas chromatography. As a result, a resultant product having a purity of not less than 98% was obtained from each substrate. The chemical structure of the resultant product was determined by NMR, two-dimensional NMR, GC-MS analysis and the like. As a result, 10-hydroxy-hexadecanoic acid having a purity of not less than 98% could be obtained from cis-9-hexadecenoic acid (pulmitoleic acid). 12-Hydroxy-octadecanoic acid having a purity of not less than 98% could be obtained from cis-11-octadecenoic acid (cis-vaccenic acid). 13-Hydroxy-cis-9-octadecenoic acid having a purity of not less than 98% could be obtained from cis-9,cis-12-octadecadienoic acid (linoleic acid). 13-Hydroxy-cis-6,cis-9-octadecadienoic acid having a purity of not less than 98% could be obtained from cis-6,cis-9,cis-12-octadecatrienoic acid (γ-linolenic acid). 13-hydroxy-cis-9,cis-15-octadecadienoic acid having a purity of not less than 98% could be obtained from cis-9,cis-12,cis-15-octadecatrienoic acid (α-linolenic acid). 13-Hydroxy-cis-6,cis-9,cis-15-octadecatrienoic acid having a purity of not less than 98% could be obtained from cis-6,cis-9,cis-12,cis-15-octadecatetraenoic acid (stearidonic acid). 12-Hydroxy-cis-14-eicosenoic acid and 15-hydroxy-cis-11-eicosenoic acid having a purity of not less than 98% could be obtained from cis-11,cis-14-eicosadienoic acid. 12-Hydroxy-cis-14,cis-17-eicosadienoic acid and 15-hydroxy-cis-11,cis-17-eicosadienoic acid having a purity of not less than 98% could be obtained from cis-11,cis-14, cis-17-eicosatrienoic acid. 15-Hydroxy-cis-8,cis-11-eicosadienoic acid and 12-hydroxy-cis-8,cis-14-eicosadienoic acid having a purity of not less than 98% could be obtained from cis-8,cis-11,cis-14-eicosatrienoic acid (dihomo-γ-linolenic acid). 12-Hydroxy-cis-5,cis-8-eicosadienoic acid having a purity of not less than 98% could be obtained from cis-5, cis-8,cis-11-eicosatrienoic acid (mead acid). 12-Hydroxy-cis-8,cis-14,cis-17-eicosatrienoic acid and 15-hydroxy-cis-8,cis-11,cis-17-eicosatrienoic acid having a purity of not less than 98% could be obtained from cis-8,cis-11,cis-14,cis-17-eicosatetraenoic acid. 15-Hydroxy-cis-5,cis-8,cis-11-eicosatrienoic acid and 12-hydroxy-cis-5,cis-8,cis-14-eicosatrienoic acid having a purity of not less than 98% could be obtained from cis-5,cis-8,cis-11,cis-14-eicosatetraenoic acid (arachidonic acid). 10,13-Dihydroxy-octadecanoic acid having a purity of not less than 98% could be obtained from 10-hydroxy-cis-12-octadecenoic acid. 10,13-Dihydroxy-cis-6-octadecenoic acid having a purity of not less than 98% could be obtained from 10-hydroxy-cis-6,cis-12-octadecadienoic acid. 10,13-Dihydroxy-cis-15-octadecenoic acid having a purity of not less than 98% could be obtained from 10-hydroxy-cis-12,cis-15-octadecadienoic acid. 10,13-Dihydroxy-cis-6,cis-15-octadecadienoic acid having a purity of not less than 98% could be obtained from 10-hydroxy-cis-6,cis-12,cis-15-octadecatrienoic acid. 10-Oxo-13-hydroxy-octadecanoic acid having a purity of not less than 98% could be obtained from 10-oxo-cis-12-octadecenoic acid. 10-Oxo-13-hydroxy-cis-6-octadecenoic acid having a purity of not less than 98% could be obtained from 10-oxo-cis-6,cis-12-octadecadienoic acid. 10-Oxo-13-hydroxy-cis-15-octadecenoic acid having a purity of not less than 98% could be obtained from 10-oxo-cis-12,cis-15-octadecadienoic acid. 10-Oxo-13-hydroxy-cis-6,cis-15-octadecadienoic acid having a purity of not less than 98% could be obtained from 10-oxo-cis-6,cis-12,cis-15-octadecatrienoic acid. 13-Hydroxy-cis-5,cis-9-octadecadienoic acid having a purity of not less than 98% could be obtained from cis-5, cis-9,cis-12-octadecatrienoic acid (pinolenic acid). 13-Hydroxy-trans-5,cis-9-octadecadienoic acid having a purity of not less than 98% could be obtained from trans-5,cis-9,cis-12-octadecatrienoic acid (columbinic acid). 15-Hydroxy-cis-5,cis-11-eicosadienoic acid having a purity of not less than 98% could be obtained from cis-5,cis-11,cis-14-eicosatrienoic (Sciadonic acid). 15-Hydroxy-cis-5,cis-11,cis-17-eicosatrienoic acid having a purity of not less than 98% could be obtained from cis-5,cis-11,cis-14,cis-17-eicosatetraenoic acid (juniperonic acid). 14-Hydroxy-cis-4,cis-7,cis-10,cis-16,cis-19-docosapentaenoic acid having a purity of not less than 98% could be obtained from cis-4,cis-7,cis-10,cis-13,cis-16,cis-19-docosahexaenoic acid (DHA). 10-Hydroxy-tetradecanoic acid having a purity of not less than 98% could be obtained from cis-9-tetradecenoic acid (myristoleic acid).

Example 6

Production of Oxo Fatty Acid from Hydroxylated Fatty Acid by Using Dehydrogenase (CLA-DH) Expressed in *Escherichia coli*

An oxo fatty acid production test from hydroxylated fatty acid was performed using purified dehydrogenase (CLA-DH) derived from *L. plantarum* FERM BP-10549 strain obtained by the method described in JP-A-2007-259712 or the method described in WO/2013/168310. The reaction mixture was adjusted to the total amount of 1 ml with 50 mM potassium phosphate buffer (pH 8.0) containing purified dehydrogenase (enzyme amount 83 μg), 0.5 mM NAD$^+$, 0.5 mg hydroxylated fatty acid. The reaction was performed by anaerobically shaking at 37° C., 120 rpm for 24 hr in the presence of an oxygen adsorbent Anaeropack (Mitsubishi Chemical Corporation). After the reaction, lipid was extracted by Bligh-Dyer method from the reaction mixture. The extract was methylesterified and production of oxo fatty acid was evaluated by gas chromatography. As a result, production of oxo fatty acid 13-oxo-cis-9-octadecenoic acid (0.01 mg) was confirmed when hydroxylated fatty acid 13-hydroxy-cis-9-octadecenoic acid was used as a substrate. Production of 13-oxo-cis-9,cis-15-octadecadienoic acid (0.02 mg) was confirmed when 13-hydroxy-cis-9,cis-15-octadecadienoic acid was used as a substrate, and production of 13-oxo-cis-6,cis-9-octadecadienoic acid (0.06 mg) was confirmed when 13-hydroxy-cis-6,cis-9-octadecadienoic acid was used as a substrate.

Using a similar method, the resultant product oxo fatty acid can be obtained by using each hydroxylated fatty acid as a substrate.

Example 7

Production of Oxo Fatty Acid from Hydroxylated Fatty Acid by Using Anhydrous Chromic Acid ($CrO_3$)

To anhydrous chromic acid (2.67 g) were added sulfuric acid (2.3 ml) and water (7.7 ml), and acetone (90 ml) was added thereto to give a chromic acid solution. 2 g of hydroxylated fatty acid and 40 ml of acetone were added into an Erlenmeyer flask, and the above-mentioned chromic acid solution was added drop by drop on ice while stirring the mixture with a stirrer. When the solution turned from blue to the color of powdered green tea, the dropwise addition of the chromic acid solution was stopped and the reaction was quenched with isopropyl alcohol. The precipitated sediment was filtered with a filter paper and placed in a partitioning funnel. Diethyl ether (150 ml) and Milli Q water (300 ml) were further added and the mixture was shaken well. The diethyl ether layer was washed several times with Milli Q water. To the diethyl ether layer after washing was added an appropriate amount of sodium sulfate (anhydrous), the mixture was stirred, and the residual water was removed. The anhydrous sodium sulfate added was filtered off with a filter paper, the obtained diethyl ether layer was concentrated in a rotary evaporator, and the reaction product (oxo fatty acid) and an unreacted substrate were extracted.

Example 8

Purification of Resultant Product from Extracts (Mixture Containing Substrate and Resultant Product (Oxo Fatty Acid)) Obtained in Examples 6, 7

The extracts (mixture containing substrate and resultant product (oxo fatty acid)) obtained in Examples 6, 7 were subjected to moderate-pressure chromatography, a solution that came out from the column was recovered in fractions. The recovered each fraction was analyzed by LC/MS and gas chromatography, fractions containing hydroxylated fatty acid alone were collected and concentrated by a rotary evaporator. A part of the obtained final resultant product was methylesterified, and the purity of oxo fatty acid was evaluated by gas chromatography. As a result, oxo fatty acid having a purity of not less than 98% was obtained from each substrate. The chemical structure of the resultant product was determined by NMR, two-dimensional NMR, GC-MS analysis and the like. As a result, 13-oxo-cis-9-octadecenoic acid having a purity of not less than 98% could be obtained from 13-hydroxy-cis-9-octadecenoic acid. 13-Oxo-cis-6,cis-9-octadecadienoic acid having a purity of not less than 98% could be obtained from 13-hydroxy-cis-6,cis-9-octadecadienoic acid. 13-Oxo-cis-9,cis-15-octadecadienoic acid having a purity of not less than 98% could be obtained from 13-hydroxy-cis-9,cis-15-octadecadienoic acid.

Using a similar method, 10-oxo-hexadecanoic acid having a purity of not less than 98% can be obtained from 10-hydroxy-hexadecanoic acid. 12-Oxo-octadecanoic acid having a purity of not less than 98% can be obtained from 12-hydroxy-octadecanoic acid. 13-Oxo-cis-6,cis-9,cis-15-octadecatrienoic acid having a purity of not less than 98% can be obtained from 13-hydroxy-cis-6,cis-9,cis-15-octadecatrienoic acid. 15-Oxo-cis-11-eicosenoic acid having a purity of not less than 98% can be obtained from 15-hydroxy-cis-11-eicosenoic acid. 12-Oxo-cis-14-eicosenoic acid having a purity of not less than 98% can be obtained from 12-hydroxy-cis-14-eicosenoic acid. 12-Oxo-cis-14,cis-17-eicosadienoic acid having a purity of not less than 98% can be obtained from 12-hydroxy-cis-14,cis-17-eicosadienoic acid. 15-Oxo-cis-11,cis-17-eicosadienoic acid having a purity of not less than 98% can be obtained from 15-hydroxy-cis-11,cis-17-eicosadienoic acid. 15-Oxo-cis-8,cis-11-eicosadienoic acid having a purity of not less than 98% can be obtained from 15-hydroxy-cis-8,cis-11-eicosadienoic acid. 12-Oxo-cis-8,cis-14-eicosadienoic acid having a purity of not less than 98% can be obtained from 12-hydroxy-cis-8,cis-14-eicosadienoic acid. 12-Oxo-cis-5,cis-8-eicosadienoic acid having a purity of not less than 98% can be obtained from 12-hydroxy-cis-5,cis-8-eicosadienoic acid. 12-Oxo-cis-8,cis-14,cis-17-eicosatrienoic acid having a purity of not less than 98% can be obtained from 12-hydroxy-cis-8,cis-14,cis-17-eicosatrienoic acid. 15-Oxo-cis-8,cis-11,cis-17-eicosatrienoic acid having a purity of not less than 98% can be obtained from 15-hydroxy-cis-8,cis-11,cis-17-eicosatrienoic acid. 15-Oxo-cis-5,cis-8,cis-11-eicosatrienoic acid having a purity of not less than 98% can be obtained from 15-hydroxy-cis-5,cis-8,cis-11-eicosatrienoic acid. 12-Oxo-cis-5,cis-8,cis-14-eicosatrienoic acid having a purity of not less than 98% can be obtained from 12-hydroxy-cis-5,cis-8,cis-14-eicosatrienoic acid. 10,13-Dioxo-octadecanoic acid having a purity of not less than 98% can be obtained from 10,13-dihydroxy-octadecanoic acid or 10-oxo-13-hydroxy-octadecanoic acid. 10,13-Dioxo-cis-6-octadecenoic acid having a purity of not less than 98% can be obtained from 10,13-dihydroxy-cis-6-octadecenoic acid or 10-oxo-13-hydroxy-cis-6-octadecenoic acid. 10,13-Dioxo-cis-15-octadecenoic acid having a purity of not less than 98% can be obtained from 10,13-dihydroxy-cis-15-octadecenoic acid or 10-oxo-13-hydroxy-cis-15-octadecenoic acid. 10,13-Dioxo-cis-6,cis-15-octadecadienoic acid having a purity of not less than 98% can be obtained from 10,13-dihydroxy-cis-6,cis-15-octadecadienoic acid or 10-oxo-13-hydroxy-cis-6,cis-15-octadecadienoic acid. 13-Oxo-cis-5,cis-9-octadecadienoic acid having a purity of not less than 98% can be obtained from 13-hydroxy-cis-5,cis-9-octadecadienoic acid. 13-Oxo-trans-5,cis-9-octadecadienoic acid having a purity of not less than 98% can be obtained from 13-hydroxy-trans-5,cis-9-octadecadienoic acid. 15-Oxo-cis-5,cis-11-eicosadienoic acid having a purity of not less than 98% can be obtained from 15-hydroxy-cis-5,cis-11-eicosadienoic acid. 15-Oxo-cis-5,cis-11,cis-17-eicosatrienoic acid having a purity of not less than 98% can be obtained from 15-hydroxy-cis-5,cis-11,cis-17-eicosatrienoic acid. 14-Oxo-cis-4,cis-7,cis-10,cis-16,cis-19-docosapentaenoic acid having a purity of not less than 98% can be obtained from 14-hydroxy-cis-4,cis-7,cis-10,cis-16,cis-19-docosapentaenoic acid. 10-Oxo-tetradecanoic acid having a purity of not less than 98% can be obtained from 10-hydroxy-tetradecanoic acid.

Example 9

Measurement of Activity as Agonist of Nuclear Receptors PPARα and PPARγ

The PPARα,γ activation ability of the PPAR ligand of the present invention was measured in reference to Nobuyuki Takahashi et al., FEBS Letters 514 (2002) p. 315-322, "Dual action of isoprenols from herbal medicines on both PPAR-gamma and PPARalpha in 3T3-L1 adipocytes and HepG2 hepatocytes.", the section of Material and Methods "Reporter plasmids and luciferase assays". To be specific, PPARα,γ ligand activity was measured by a reporter assay that evaluates binding to a fusion protein of PPAR ligand binding region and GAL4 DNA binding region and target gene activation, based on the expression of luciferase. Specifically, a plasmid comprising a DNA encoding a fusion protein of PPARα,γ ligand binding region and GAL4 DNA binding region and a reporter plasmid wherein luciferase linked to GAL4 bound DNA sequence were introduced into CV-1 cell, a ligand described below was added to the cell, the cell was incubated and the luciferase activity was detected.

The concentration of the sample was adjusted with ethanol. Ethanol was used as a negative control, and PPARα,γ ligands GW7647 (10 nM) and troglitazone (5 µM) were used as a positive control.

Figure 2:
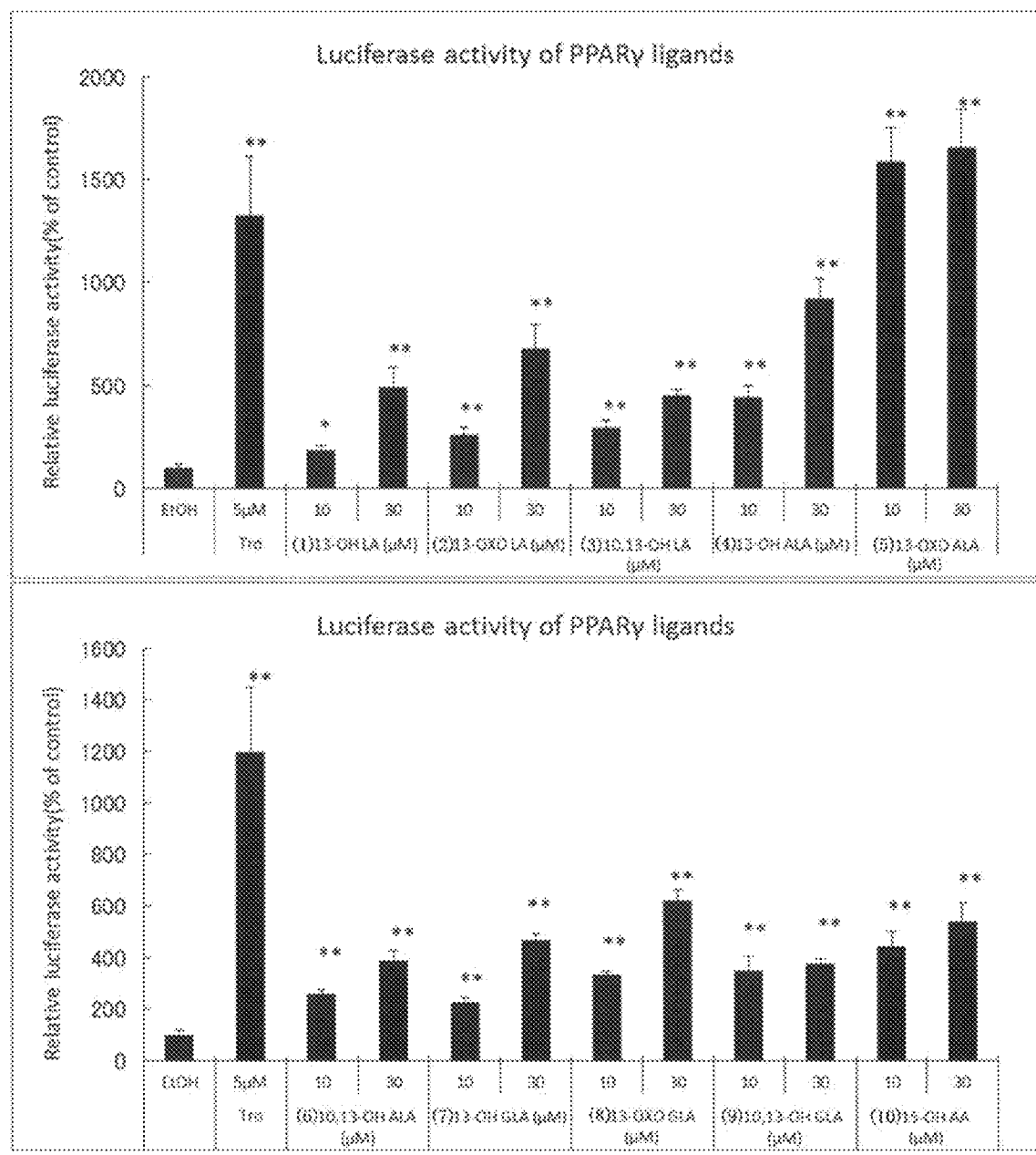
FIG. 2 shows the results of PPARγ agonist activity of rare fatty acids derived from linoleic acid, α-linolenic acid, γ-linolenic acid, and arachidonic acid. EtOH shows a negative control (ethanol addition), and Tro shows a positive control (PPARγ agonist addition). The vertical axis shows relative luciferase activity.

The PPARα, γ ligand activity data of representative hydroxylated fatty acid, oxo fatty acid, (1) 13-hydroxy-cis-9-octadecenoic acid (indicated as "13-OH LA"), (2) 13-oxo-cis-9-octadecenoic acid (indicated as "13-OXO LA"), (3) 10,13-dihydroxy-octadecanoic acid (indicated as "10,13-OH LA"), (4) 13-hydroxy-cis-9,cis-15-octadecadienoic acid (indicated as "13-OH ALA"), (5) 13-oxo-cis-9,cis-15-octadecadienoic acid (indicated as "13-OXO ALA"), (6) 10,13-dihydroxy-cis-15-octadecenoic acid (indicated as "10,13-OH ALA") (7) 13-hydroxy-cis-6,cis-9-octadecadienoic acid (indicated as "13-OH GLA"), (8) 13-oxo-cis-6,cis-9-octadecadienoic acid (indicated as "13-OXO GLA"), (9) 10,13-dihydroxy-cis-6-octadecenoic acid (indicated as "10,13-OH GLA"), (10) 15-hydroxy-cis-5,cis-8,cis-11-eicosatrienoic acid (indicated as "15-OH AA") are shown in FIG. 1 and FIG. 2. Of these, rare fatty acids of (4), (6), (8) and (9) are novel fatty acids.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

INDUSTRIAL APPLICABILITY

According to the method of the present invention, various hydroxylated fatty acids and oxo fatty acids can be produced, and therefore, the hydroxylated fatty acids and oxo fatty acids can be applied to various field of medicament, food and the like. In addition, according to the method of the present invention, novel rare fatty acid can be produced, which is extremely useful.

This application is based on a patent application No. 2014-011855 filed in Japan (filing date: Jan. 24, 2014), the contents of which are incorporated in full herein.

The invention claimed is:

1. 14-Hydroxy-cis-4,cis-7,cis-10,cis-16,cis-19-docosapentaenoic acid.

2. A method of producing 14-hydroxy-cis-4,cis-7,cis-10,cis-16,cis-19-docosapentaenoic acid, comprising incubating under suitable conditions cis-4,cis-7,cis-10,cis-13,cis-16,cis-19-docosahexaenoic acid with a hydratase of any of the following (a)-(c):
   (a) the protein consisting of the amino acid sequence shown in SEQ ID NO: 2,
   (b) a protein comprising an amino acid sequence wherein one to twenty amino acids in the amino acid sequence shown in SEQ ID NO: 2 are deleted and/or substituted and/or inserted and/or added, and having an enzyme activity that catalyzes a hydration reaction, and
   (c) a protein encoded by a nucleotide sequence that hybridizes to a nucleic acid consisting of a nucleotide sequence complementary to the nucleotide sequence shown in SEQ ID NO: 1 under conditions comprising a wash in 0.1×SSC, 0.1% SDS at 68° C., and having an enzyme activity that catalyzes a hydration reaction.

3. A method of producing 14-hydroxy-cis-4,cis-7,cis-10,cis-16,cis-19-docosapentaenoic acid according to claim 2, wherein the hydratase is the protein consisting of the amino acid sequence shown in SEQ ID NO: 2.

4. A method of producing 14-hydroxy-cis-4,cis-7,cis-10,cis-16,cis-19-docosapentaenoic acid according to claim 2, wherein the hydratase is a protein comprising an amino acid sequence wherein one to twenty amino acids in the amino acid sequence shown in SEQ ID NO: 2 are deleted and/or substituted and/or inserted and/or added, and having an enzyme activity that catalyzes a hydration reaction.

5. A method of producing 14-hydroxy-cis-4,cis-7,cis-10,cis-16,cis-19-docosapentaenoic acid according to claim 2, wherein the hydratase is a protein encoded by a nucleotide sequence that hybridizes to a nucleic acid consisting of a nucleotide sequence complementary to the nucleotide sequence shown in SEQ ID NO: 1 under conditions comprising a wash in 0.1×SSC, 0.1% SDS at 68° C., and having an enzyme activity that catalyzes a hydration reaction.

* * * * *

SEQUENCE LISTING

<160> NUMBER OF SEQ ID NOS: 4

<210> SEQ ID NO 1
<211> LENGTH: 1773
<212> TYPE: DNA
<213> ORGANISM: Lactobacillus acidophilus
<220> FEATURE:
<221> NAME/KEY: CDS
<222> LOCATION: (1)..(1773)

<400> SEQUENCE: 1

```
atg cat tat agt agt ggt aat tat gaa gct ttt gta aac gca agt aaa       48
Met His Tyr Ser Ser Gly Asn Tyr Glu Ala Phe Val Asn Ala Ser Lys
1               5                   10                  15 cct aag gat gtc gat cag aag tcc gca tat ctt gtt ggt tca ggt ttg       96
Pro Lys Asp Val Asp Gln Lys Ser Ala Tyr Leu Val Gly Ser Gly Leu
            20                  25                  30 gca tcg ctt gct agt gct gta ttt tta att cgt gat ggt cac atg aag      144
Ala Ser Leu Ala Ser Ala Val Phe Leu Ile Arg Asp Gly His Met Lys
        35                  40                  45 ggt gat aga att cat atc ctt gaa gaa ttg agc ctt cca ggt ggt tca      192
Gly Asp Arg Ile His Ile Leu Glu Glu Leu Ser Leu Pro Gly Gly Ser
    50                  55                  60 atg gat ggg atc tat aat aag caa aaa gaa agc tac atc att cgt ggt      240
Met Asp Gly Ile Tyr Asn Lys Gln Lys Glu Ser Tyr Ile Ile Arg Gly
65                  70                  75                  80 ggt cgt gaa atg gaa gcc cat ttt gaa tgc ttg tgg gac ttg ttt aga      288
Gly Arg Glu Met Glu Ala His Phe Glu Cys Leu Trp Asp Leu Phe Arg
                85                  90                  95 tcg att cca tca gct gaa aat aaa gat gaa tcg gtc ctg gat gaa ttt      336
Ser Ile Pro Ser Ala Glu Asn Lys Asp Glu Ser Val Leu Asp Glu Phe
            100                 105                 110 tac cgt tta aat aga aaa gat cca agt ttc gca aag act cgt gtc att      384
Tyr Arg Leu Asn Arg Lys Asp Pro Ser Phe Ala Lys Thr Arg Val Ile
        115                 120                 125 gtt aac cgc gga cat gaa ctt cca act gac ggt caa tta ctt ctt act      432
Val Asn Arg Gly His Glu Leu Pro Thr Asp Gly Gln Leu Leu Leu Thr
    130                 135                 140 ccc aag gct gtt aaa gaa att att gat ctt tgc tta act cct gaa aaa      480
Pro Lys Ala Val Lys Glu Ile Ile Asp Leu Cys Leu Thr Pro Glu Lys
145                 150                 155                 160 gat tta caa aat aaa aaa att aat gaa gtc ttt agt aaa gaa ttt ttt      528
Asp Leu Gln Asn Lys Lys Ile Asn Glu Val Phe Ser Lys Glu Phe Phe
                165                 170                 175 gaa tca aac ttc tgg ctt tac tgg tca acg atg ttt gcc ttt gag cca      576
Glu Ser Asn Phe Trp Leu Tyr Trp Ser Thr Met Phe Ala Phe Glu Pro
            180                 185                 190 tgg gca agt gcg atg gaa atg cgt cgt tac tta atg cgt ttt gtt caa      624
Trp Ala Ser Ala Met Glu Met Arg Arg Tyr Leu Met Arg Phe Val Gln
        195                 200                 205 cac gtt tct aca ctt aag aat tta tca tca cta cgc ttt act aag tat      672
His Val Ser Thr Leu Lys Asn Leu Ser Ser Leu Arg Phe Thr Lys Tyr
    210                 215                 220 aac caa tat gaa tca tta att tca cca atg gtt aaa tac ttg aaa gat      720
Asn Gln Tyr Glu Ser Leu Ile Ser Pro Met Val Lys Tyr Leu Lys Asp
225                 230                 235                 240 cgc ggc gtg caa ttc cat tac aac acc gtt gtt gat aat atc ttt gtt      768
```

```
                Arg Gly Val Gln Phe His Tyr Asn Thr Val Val Asp Asn Ile Phe Val
                                245                 250                 255 aac cgt tca aat ggt gaa aag att gct aag caa att ctt tta act gaa         816
Asn Arg Ser Asn Gly Glu Lys Ile Ala Lys Gln Ile Leu Leu Thr Glu
                260                 265                 270 aac ggt gaa aaa aag agc atc gat tta aca gaa aat gac ctc gtc ttc         864
Asn Gly Glu Lys Lys Ser Ile Asp Leu Thr Glu Asn Asp Leu Val Phe
                275                 280                 285 gtt act aac ggt tca att act gaa agt aca act tat ggt gat aac ttg         912
Val Thr Asn Gly Ser Ile Thr Glu Ser Thr Thr Tyr Gly Asp Asn Leu
            290                 295                 300 cac cca gct tct gag gaa cat aaa tta ggt gct act tgg aaa tta tgg         960
His Pro Ala Ser Glu Glu His Lys Leu Gly Ala Thr Trp Lys Leu Trp
305                 310                 315                 320 caa aac ttg gca gcg caa gat gat gac ttc ggt cac cca gat gtc ttc        1008
Gln Asn Leu Ala Ala Gln Asp Asp Asp Phe Gly His Pro Asp Val Phe
                325                 330                 335 tgc aag gat att cca aag gct aac tgg gta atg tct gct aca att act        1056
Cys Lys Asp Ile Pro Lys Ala Asn Trp Val Met Ser Ala Thr Ile Thr
                340                 345                 350 ttt aag aat aat gat att gtg cca ttc att gaa gca gtt aat aag aag        1104
Phe Lys Asn Asn Asp Ile Val Pro Phe Ile Glu Ala Val Asn Lys Lys
                355                 360                 365 gat cca cac agc ggc tca att gta act agt ggg cct act acg att aag        1152
Asp Pro His Ser Gly Ser Ile Val Thr Ser Gly Pro Thr Thr Ile Lys
            370                 375                 380 gat tct aac tgg cta ctt ggt tat tca atc agt cgt cag cct cac ttt        1200
Asp Ser Asn Trp Leu Leu Gly Tyr Ser Ile Ser Arg Gln Pro His Phe
385                 390                 395                 400 gaa gca caa aag cct aac gaa ttg att gta tgg ctt tat ggt ttg ttc        1248
Glu Ala Gln Lys Pro Asn Glu Leu Ile Val Trp Leu Tyr Gly Leu Phe
                405                 410                 415 tca gac acc aaa ggt aac tat gtt gaa aag act atg cct gac tgt aac        1296
Ser Asp Thr Lys Gly Asn Tyr Val Glu Lys Thr Met Pro Asp Cys Asn
                420                 425                 430 ggt att gaa tta tgt gaa gaa tgg ctt tac cac atg ggt gtt cct gaa        1344
Gly Ile Glu Leu Cys Glu Glu Trp Leu Tyr His Met Gly Val Pro Glu
                435                 440                 445 gaa aga atc cca gaa atg gct tca gct gct acg act att cca gca cac        1392
Glu Arg Ile Pro Glu Met Ala Ser Ala Ala Thr Thr Ile Pro Ala His
450                 455                 460 atg cca tat att act tca tac ttc atg cca aga gca tta ggc gac aga        1440
Met Pro Tyr Ile Thr Ser Tyr Phe Met Pro Arg Ala Leu Gly Asp Arg
465                 470                 475                 480 ccc aag gtt gtg cca gac cac tca aag aac ttg gcc ttc att ggt aac        1488
Pro Lys Val Val Pro Asp His Ser Lys Asn Leu Ala Phe Ile Gly Asn
                485                 490                 495 ttt gct gaa acg cca aga gac act gtc ttt acc act gaa tac tct gtc        1536
Phe Ala Glu Thr Pro Arg Asp Thr Val Phe Thr Thr Glu Tyr Ser Val
                500                 505                 510 aga act gcg atg gaa gct gta tac acc ttg ctt aac att gat cgt ggt        1584
Arg Thr Ala Met Glu Ala Val Tyr Thr Leu Leu Asn Ile Asp Arg Gly
            515                 520                 525 gtg cca gaa gta ttt gca tct gcc ttc gat gtc aga atg ctc atg aac        1632
Val Pro Glu Val Phe Ala Ser Ala Phe Asp Val Arg Met Leu Met Asn
            530                 535                 540 gca atg tac tac ttg aat gat caa aag aag ctt gaa gat ctt gat ttg        1680
Ala Met Tyr Tyr Leu Asn Asp Gln Lys Lys Leu Glu Asp Leu Asp Leu
545                 550                 555                 560
```

```
cct att gct gaa aag ttg gca att aag ggg atg ctc aag aaa gtt aag    1728
Pro Ile Ala Glu Lys Leu Ala Ile Lys Gly Met Leu Lys Lys Val Lys
                565                 570                 575 ggc act tat ata gag gaa ttg ctt aag aag tat aag ttg gtt tag        1773
Gly Thr Tyr Ile Glu Glu Leu Leu Lys Lys Tyr Lys Leu Val
                580                 585                 590
```

<210> SEQ ID NO 2
<211> LENGTH: 590
<212> TYPE: PRT
<213> ORGANISM: Lactobacillus acidophilus

<400> SEQUENCE: 2

```
Met His Tyr Ser Ser Gly Asn Tyr Glu Ala Phe Val Asn Ala Ser Lys
1               5                   10                  15

Pro Lys Asp Val Asp Gln Lys Ser Ala Tyr Leu Val Gly Ser Gly Leu
                20                  25                  30

Ala Ser Leu Ala Ser Ala Val Phe Leu Ile Arg Asp Gly His Met Lys
            35                  40                  45

Gly Asp Arg Ile His Ile Leu Glu Glu Leu Ser Leu Pro Gly Gly Ser
        50                  55                  60

Met Asp Gly Ile Tyr Asn Lys Gln Lys Glu Ser Tyr Ile Ile Arg Gly
65                  70                  75                  80

Gly Arg Glu Met Glu Ala His Phe Glu Cys Leu Trp Asp Leu Phe Arg
                85                  90                  95

Ser Ile Pro Ser Ala Glu Asn Lys Asp Glu Ser Val Leu Asp Glu Phe
                100                 105                 110

Tyr Arg Leu Asn Arg Lys Asp Pro Ser Phe Ala Lys Thr Arg Val Ile
            115                 120                 125

Val Asn Arg Gly His Glu Leu Pro Thr Asp Gly Gln Leu Leu Leu Thr
        130                 135                 140

Pro Lys Ala Val Lys Glu Ile Ile Asp Leu Cys Leu Thr Pro Glu Lys
145                 150                 155                 160

Asp Leu Gln Asn Lys Lys Ile Asn Glu Val Phe Ser Lys Glu Phe Phe
                165                 170                 175

Glu Ser Asn Phe Trp Leu Tyr Trp Ser Thr Met Phe Ala Phe Glu Pro
            180                 185                 190

Trp Ala Ser Ala Met Glu Met Arg Arg Tyr Leu Met Arg Phe Val Gln
        195                 200                 205

His Val Ser Thr Leu Lys Asn Leu Ser Ser Leu Arg Phe Thr Lys Tyr
    210                 215                 220

Asn Gln Tyr Glu Ser Leu Ile Leu Pro Met Val Lys Tyr Leu Lys Asp
225                 230                 235                 240

Arg Gly Val Gln Phe His Tyr Asn Thr Val Val Asp Asn Ile Phe Val
                245                 250                 255

Asn Arg Ser Asn Gly Glu Lys Ile Ala Lys Gln Ile Leu Leu Thr Glu
            260                 265                 270

Asn Gly Glu Lys Lys Ser Ile Asp Leu Thr Glu Asn Asp Leu Val Phe
        275                 280                 285

Val Thr Asn Gly Ser Ile Thr Glu Ser Thr Thr Tyr Gly Asp Asn Leu
    290                 295                 300

His Pro Ala Ser Glu Glu His Lys Leu Gly Ala Thr Trp Lys Leu Trp
305                 310                 315                 320

Gln Asn Leu Ala Ala Gln Asp Asp Phe Gly His Pro Asp Val Phe
                325                 330                 335
```

Cys Lys Asp Ile Pro Lys Ala Asn Trp Val Met Ser Ala Thr Ile Thr
            340                 345                 350

Phe Lys Asn Asn Asp Ile Val Pro Phe Ile Glu Ala Val Asn Lys Lys
            355                 360                 365

Asp Pro His Ser Gly Ser Ile Val Thr Ser Gly Pro Thr Thr Ile Lys
            370                 375                 380

Asp Ser Asn Trp Leu Leu Gly Tyr Ser Ile Ser Arg Gln Pro His Phe
385                 390                 395                 400

Glu Ala Gln Lys Pro Asn Glu Leu Ile Val Trp Leu Tyr Gly Leu Phe
                405                 410                 415

Ser Asp Thr Lys Gly Asn Tyr Val Glu Lys Thr Met Pro Asp Cys Asn
                420                 425                 430

Gly Ile Glu Leu Cys Glu Glu Trp Leu Tyr His Met Gly Val Pro Glu
                435                 440                 445

Glu Arg Ile Pro Glu Met Ala Ser Ala Ala Thr Thr Ile Pro Ala His
            450                 455                 460

Met Pro Tyr Ile Thr Ser Tyr Phe Met Pro Arg Ala Leu Gly Asp Arg
465                 470                 475                 480

Pro Lys Val Val Pro Asp His Ser Lys Asn Leu Ala Phe Ile Gly Asn
                485                 490                 495

Phe Ala Glu Thr Pro Arg Asp Thr Val Phe Thr Thr Glu Tyr Ser Val
                500                 505                 510

Arg Thr Ala Met Glu Ala Val Tyr Thr Leu Leu Asn Ile Asp Arg Gly
            515                 520                 525

Val Pro Glu Val Phe Ala Ser Ala Phe Asp Val Arg Met Leu Met Asn
            530                 535                 540

Ala Met Tyr Tyr Leu Asn Asp Gln Lys Lys Leu Glu Asp Leu Asp Leu
545                 550                 555                 560

Pro Ile Ala Glu Lys Leu Ala Ile Lys Gly Met Leu Lys Lys Val Lys
                565                 570                 575

Gly Thr Tyr Ile Glu Glu Leu Leu Lys Lys Tyr Lys Leu Val
            580                 585                 590

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
acacatatgc attatagtag tggtaat                                      27

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4
aaactcgagc taaaccaact tatacttct                                    29